United States Patent
Yokoyama et al.

(10) Patent No.: US 9,564,600 B2
(45) Date of Patent: Feb. 7, 2017

(54) COMPOUND HAVING AN INDOLOCARBAZOLE RING STRUCTURE AND ORGANIC ELECTROLUMINESCENT DEVICE

(75) Inventors: Norimasa Yokoyama, Tokyo (JP); Makoto Nagaoka, Ibaraki (JP); Sawa Izumi, Tokyo (JP); Hiroshi Ookuma, Tokyo (JP); Shuichi Hayashi, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 683 days.

(21) Appl. No.: 14/000,406

(22) PCT Filed: Feb. 14, 2012

(86) PCT No.: PCT/JP2012/053336
§ 371 (c)(1),
(2), (4) Date: Aug. 20, 2013

(87) PCT Pub. No.: WO2012/114928
PCT Pub. Date: Aug. 30, 2012

(65) Prior Publication Data
US 2014/0124756 A1    May 8, 2014

(30) Foreign Application Priority Data
Feb. 22, 2011  (JP) .................. 2011-035287

(51) Int. Cl.
*H01L 51/00* (2006.01)
*C07D 487/04* (2006.01)
(Continued)

(52) U.S. Cl.
CPC .......... *H01L 51/006* (2013.01); *C07D 487/04* (2013.01); *C09K 11/06* (2013.01); *H01L 51/0061* (2013.01);
(Continued)

(58) Field of Classification Search
CPC .................. C07D 487/04; H05B 33/10; C09K 2211/1007; C09K 2211/1011; C09K 2211/1014; C09K 2211/1029; C09K 2211/1037; C09K 2211/1088; C09K 2211/1092; C09K 11/06; H01L 51/006; H01L 51/0061; H01L 51/0067; H01L 51/0071; H01L 51/0072; H01L 51/0073; H01L 51/5056
(Continued)

(56) References Cited

U.S. PATENT DOCUMENTS 5,639,914 A    6/1997    Tomiyama et al.
5,707,747 A    1/1998    Tomiyama et al.
(Continued)

FOREIGN PATENT DOCUMENTS

JP    8-048656    2/1996
JP    11-167215    6/1999
(Continued)

OTHER PUBLICATIONS

Machine translation of KR 10-2011-0016047, Je et al, Feb. 7, 2011.*
(Continued)

*Primary Examiner* — Frances Tischler
(74) *Attorney, Agent, or Firm* — Greenblum & Bernstein, P.L.C.

(57) ABSTRACT

A compound having an indolocarbazole ring structure is represented by the following general formula (1), and is used as a material for forming a highly efficient and highly durable organic electroluminescent device. The compound features excellent hole injection/transport capability, has electron blocking power and is highly stable in the form of a thin film.

(Continued)

8: CATHODE
7: ELECTRON INJECTION LAYER
6: ELECTRON TRANSPORTING LAYER
5: LUMINOUS LAYER
4: HOLE TRANSPORTING LAYER
3: HOLE INJECTION LAYER
2: TRANSPARENT ANODE
1: GLASS SUBSTRATE

[Chemical 1]

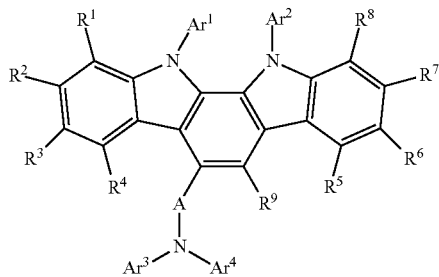

(1)

wherein,

A is a divalent aromatic hydrocarbon group or aromatic heterocyclic group, $Ar^1$ to $Ar^4$ are monovalent aromatic hydrocarbon groups or aromatic heterocyclic groups, and $R^1$ to $R^9$ are hydrogen atoms, deuterium atoms, fluorine atoms, chlorine atoms, cyano groups, nitro groups, alkyl groups, cycloalkyl groups, alkenyl groups, alkyloxy groups, cycloalkyloxy groups, aromatic hydrocarbon groups, aromatic heterocyclic groups or aryloxy groups.

3 Claims, 7 Drawing Sheets

(51) Int. Cl.

| | | |
|---|---|---|
| *C09K 11/06* | (2006.01) | |
| *H05B 33/10* | (2006.01) | |
| *H01L 51/50* | (2006.01) | |

(52) U.S. Cl.

CPC ....... *H01L 51/0071* (2013.01); *H01L 51/0072* (2013.01); *H01L 51/0073* (2013.01); *H05B 33/10* (2013.01); *C09K 2211/1007* (2013.01); *C09K 2211/1011* (2013.01); *C09K 2211/1014* (2013.01); *C09K 2211/1029* (2013.01); *C09K 2211/1037* (2013.01); *C09K 2211/1088* (2013.01); *C09K 2211/1092* (2013.01); *H01L 51/0067* (2013.01); *H01L 51/5056* (2013.01)

(58) Field of Classification Search
USPC ........................................................ 428/690
See application file for complete search history.

(56) References Cited

U.S. PATENT DOCUMENTS

| | | | |
|---|---|---|---|
| 5,792,557 | A | 8/1998 | Nakaya et al. |
| 5,843,607 | A | 12/1998 | Hu |
| 5,942,340 | A | 8/1999 | Hu |
| 7,993,760 | B2 | 8/2011 | Komori et al. |
| 8,013,330 | B2 | 9/2011 | Komori et al. |
| 8,062,769 | B2 | 11/2011 | Kai et al. |
| 2007/0112167 | A1 | 5/2007 | Li et al. |
| 2009/0295276 | A1 | 12/2009 | Asari et al. |
| 2012/0153272 | A1 | 6/2012 | Fukuzaki |

FOREIGN PATENT DOCUMENTS

| | | |
|---|---|---|
| JP | 11-176578 | 7/1999 |
| JP | 3194657 | 6/2001 |
| JP | 4564584 | 8/2010 |
| KR | 10-2011-0011578 | 2/2011 |
| KR | 10-2011-0016044 | 2/2011 |
| KR | 10-2011-0016047 | 2/2011 |
| KR | 1020110016047 | 2/2011 |
| WO | 2007/063754 | 6/2007 |
| WO | 2007/063796 | 6/2007 |
| WO | 2008/056746 | 5/2008 |
| WO | 2008/149691 | 12/2008 |

OTHER PUBLICATIONS

Taiwan Office action, mail date is May 19, 2015.
Chinese Office action in CN 201280009985.3, dated Aug. 19, 2014 along with an English translation thereof.
U.S. Appl. No. 14/008,708 to Norimasa Yokoyama et al., filed Sep. 30, 2013.
U.S. Appl. No. 14/001,560 to Norimasa Yokoyama et al., filed Aug. 26, 2013.
International Search Report issued Apr. 3, 2012 in PCT/JP2012/053336.
Japan Office action, mail date is Jul. 14, 2015.

\* cited by examiner

8: CATHODE
7: ELECTRON INJECTION LAYER
6: ELECTRON TRANSPORTING LAYER
5: LUMINOUS LAYER
4: HOLE TRANSPORTING LAYER
3: HOLE INJECTION LAYER
2: TRANSPARENT ANODE
1: GLASS SUBSTRATE

COMPOUND HAVING AN INDOLOCARBAZOLE RING STRUCTURE AND ORGANIC ELECTROLUMINESCENT DEVICE

TECHNICAL FIELD

This invention relates to a compound suited for an organic electroluminescent device which is a spontaneously light-emitting device that can be favorably used for various kinds of display devices and to an organic electroluminescent device. More specifically, the invention relates to a compound having an indolocarbazole ring structure and to an organic electroluminescent device using the same compound.

BACKGROUND ART

An organic electroluminescent device is a spontaneously light-emitting device which features higher brightness and higher legibility than those of the liquid crystal devices and enabling vivid display to be attained and has, therefore, been vigorously studied.

In 1987, C. W. Tang et al. of the Eastman Kodak Co. have developed a device of a layer-laminated structure comprising various kinds of materials to bear individual roles for emitting light, and have put an organic electroluminescent device using organic materials into a practical use. They have attempted to laminate a layer of a fluorescent material, i.e., a tris(8-hydroxyquinoline) aluminum (hereinafter abbreviated as $Alq_3$) that is capable of transporting electrons and a layer of an aromatic amine compound capable of transporting holes, to inject the electric charges of the two into the layer of the fluorescent material to emit light, and have attained a brightness of as high as 1000 $cd/m^2$ or more with a voltage of not more than 10 V.

So far, very many improvements have been made to put the organic electroluminescent device (organic EL device) to practical use. At present, the organic electroluminescent device has been widely known having a structure comprising an anode, a hole injection layer, a hole-transporting layer, a luminous layer, an electron-transporting layer, an electron injection layer and a cathode which are arranged in this order on a substrate more finely dividing their roles than ever before. The device of this kind is achieving a high efficiency and a high durability.

To further improve the luminous efficiency, attempts have been made to utilize triplet excitons and to utilize a phosphorescent luminous material as the luminous material.

In the organic EL device, the electric charges injected from the two electrodes recombine in the luminous layer to emit light. Here, what is important is how efficiently the two electric charges, i.e., holes and electrons, be handed over to the luminous layer. Upon improving the hole injection property and improving the electron blocking power for blocking the electrons injected through the cathode, it is made possible to improve the probability of recombination of the holes and the electrons. Upon confining the excitons formed in the luminous layer, further, it is allowed to attain a high luminous efficiency. Therefore, the role played by the hole-transporting material is important, and it has been urged to provide a hole-transporting material that has a hole injection property, a hole mobility, a high electron blocking power and a high durability against the electrons.

As for the life of the device, heat resistances of the materials forming the device and amorphousness thereof also play important roles. If the materials having low heat resistances are used, the materials undergo thermal decomposition due to the heat produced when the device is driven and are deteriorated. If the materials that are used have low amorphousness, the thin films thereof are crystallized in short periods of time and the device is deteriorated. Therefore, the materials used for forming the organic EL device must have high heat resistances and good amorphousness.

As the hole-transporting materials used so far for the organic EL devices, there have been known an N,N'-diphenyl-N,N'-di(α-naphthyl)benzidine (hereinafter abbreviated as NPD) and various aromatic amine derivatives (see, for example, patent documents 1 and 2).

The NPD has a favorable hole-transporting capability but has a glass transition point (Tg) which serves as an index of heat resistance of as low as 96° C. Under high temperature conditions, therefore, the device properties are deteriorated due to the crystallization. Further, some aromatic amine derivatives have high hole mobilities (e.g., $10^{-3}$ $cm^2/Vs$ or higher), namely, have excellent mobilities. Such compounds, however, have insufficient electron blocking powers; i.e., the electrons partly pass through the luminous layer, and improvement in the luminous efficiency cannot be expected.

In order to further improve the efficiency as described above, it has been desired to provide a material for the organic EL devices having a higher electron blocking power and having a higher stability and higher heat resistance in the form of a thin film.

As the material for the organic EL use improving heat stability and hole-transporting property, there have been proposed compounds having an indolocarbazole ring structure (e.g., see patent documents 3 and 4).

The devices forming the hole injection layer and the hole-transporting layer using these compounds, exhibit improved heat resistances and luminous efficiencies, which, however, are not still sufficient. Besides, they require high driving voltages and their current efficiencies are not sufficient, either. Therefore, it has been desired to lower the driving voltage and to improve the luminous efficiency.

As the compounds having the indolocarbazole ring structure, further, there have been proposed the compounds A and B having substituted indolo[2,3-a]carbazole ring structures represented by the following formulas (e.g., see patent documents 5 to 9).

[Chemical 1]

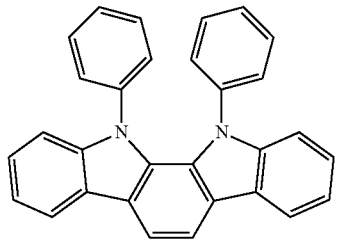

(Compound A)

-continued

[Chemical 2]

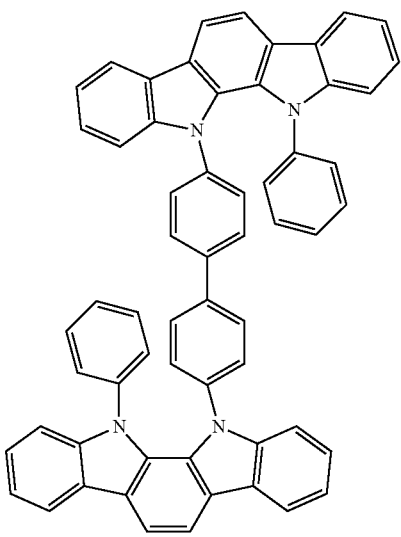

(Compound B)

However, these compounds are used as host materials of the luminous layer, but properties as the hole-transporting materials have not been quite described.

PRIOR ART DOCUMENTS

Patent Documents

Patent document 1: JP-A-8-048656
Patent document 2: Japanese Patent No. 3194657
Patent document 3: JP-A-11-167215
Patent document 4: JP-A-11-176578
Patent document 5: WO2007-063754
Patent document 6: WO2007-063796
Patent document 7: WO2008-056746
Patent document 8: WO2008-149691
Patent document 9: Japanese Patent No. 4564584

OUTLINE OF THE INVENTION

Problems that the Invention is to Solve

It is an object of the present invention to provide a novel organic compound that is used as a material for forming an organic electroluminescent device having a high efficiency and a high durability, and features excellent hole injection/transport capability, electron blocking power and a high degree of stability in the form of a thin film.

Another object of the invention is to provide an organic electroluminescent device having a high efficiency and a high durability and in which organic layers such as the charge-transporting layer and the like layers are formed by using the above-mentioned compound.

Means for Solving the Problems

The present inventors have expected that the indolocarbazole ring structure would bring about a high hole mobility, a high triplet energy level and excellent electron blocking power and would further bring about excellent heat resistance and stability in the form of a thin film, have paid attention to that the aromatic tertiary amine structure has a high hole injection/transport capability, have designed and chemically synthesized the compounds having the indolocarbazole ring structure and the aromatic tertiary amine structure, fabricated several organic electroluminescent devices on an experimental basis by using the above compound, have evaluated performance of the devices and have thus completed the invention.

According to the present invention, there is prepared a compound having an indolocarbazole ring structure and is represented by the following general formula (I),

[Chemical 3]

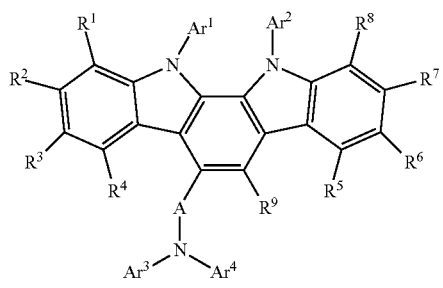

(1)

wherein,

A is a divalent aromatic hydrocarbon group or aromatic heterocyclic group, $Ar^1$, $Ar^2$, $Ar^3$ and $Ar^4$ are, respectively, monovalent aromatic hydrocarbon groups or an aromatic heterocyclic groups, wherein $Ar^3$ and $Ar^4$ may be simply bonded together, may be bonded together via a methylene group, an oxygen atom or a sulfur atom, or may be bonded to the group A to form another ring, and $R^1$ to $R^9$ are, respectively, hydrogen atoms, deuterium atoms, fluorine atoms, chlorine atoms, cyano groups, nitro groups, alkyl groups having 1 to 6 carbon atoms, cycloalkyl groups having 5 to 10 carbon atoms, alkenyl groups having 2 to 6 carbon atoms, alkyloxy groups having 1 to 6 carbon atoms, cycloalkyloxy groups having 5 to 10 carbon atoms, monovalent aromatic hydrocarbon groups, monovalent aromatic heterocyclic groups or aryloxy groups.

In the compound having the indolocarbazole ring structure of the invention represented by the above general formula (1), it is desired that A in the above general formula (1) is a phenylene group.

In the invention, further, among the compounds represented by the above general formula (1), a compound represented by the following general formula (1a) is specifically desired,

[Chemical 4]

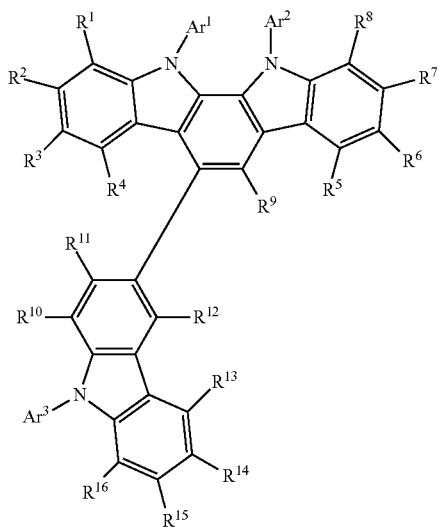

(1a)

wherein,
Ar$^1$ to Ar$^3$ and R$^1$ to R$^9$ are as defined in the above general formula (1), and
R$^{10}$ to R$^{16}$ are, respectively, hydrogen atoms, deuterium atoms, fluorine atoms, chlorine atoms, cyano groups, nitro groups, alkyl groups having 1 to 6 carbon atoms, cycloalkyl groups having 5 to 10 carbon atoms, alkenyl groups having 2 to 6 carbon atoms, alkyloxy groups having 1 to 6 carbon atoms, cycloalkyloxy groups having 5 to 10 carbon atoms, monovalent aromatic hydrocarbon groups, monovalent aromatic heterocyclic groups or aryloxy groups.

The compound of the general formula (1a) is the one in which the group A in the general formula (1) is a phenylene group and the group Ar$^4$ is bonded to the phenylene group (simply bond) to form a ring.

In the above general formula (1) according to the present invention, it is, further, desired that:
(a) Ar$^1$ and Ar$^2$ are aromatic hydrocarbon groups (monovalent);
(b) Ar$^1$ and Ar$^2$ are phenyl groups; and
(c) R$^9$ is a hydrogen atom, a deuterium atom or a phenyl group.

According to the present invention, further, there is provided an organic electroluminescent device (organic EL device) in which a laminated layer structure inclusive of at least a luminous layer is formed between a pair of electrodes, wherein the compound having the above-mentioned indolocarbazole ring structure is used for any layer that is forming the laminated layer structure.

In the organic EL device of the invention, it is desired that:
(d) The laminated layer structure includes a positive hole-transporting layer, and the compound is used for the hole-transporting layer;
(e) The laminated layer structure includes an electron blocking layer, and the compound is used for the electron blocking layer;
(f) The laminated layer structure includes a hole injection layer, and the compound is used for the hole injection layer; and
(g) The compound is used for the luminous layer.

Effects of the Invention

The compound having the indolocarbazole ring structure of the invention represented by the above general formula has such properties as:
(i) Favorable hole injection property;
(ii) Large hole mobility;
(iii) Excellent electron blocking power;
(iv) Stability in the form of a thin film; and
(v) Excellent heat resistance;
and provides excellent properties required for the organic EL devices.

The compound of the invention having the above-mentioned properties is useful as a material for constituting the layers of the organic EL device which are hole injection layer, hole-transporting layer, electron blocking layer or luminous layer, features excellent electron blocking power, and has excellent electron blocking power, favorable amorphousness, stability in the form of a thin film and excellent heat stability. Therefore, the organic EL element of the invention using the above compound has a high luminous efficiency and a high power efficiency and, therefore, offers such advantages as a low light emission start voltage, a low practical driving voltage and excellent durability.

MODES FOR CARRYING OUT THE INVENTION

Figure 1:
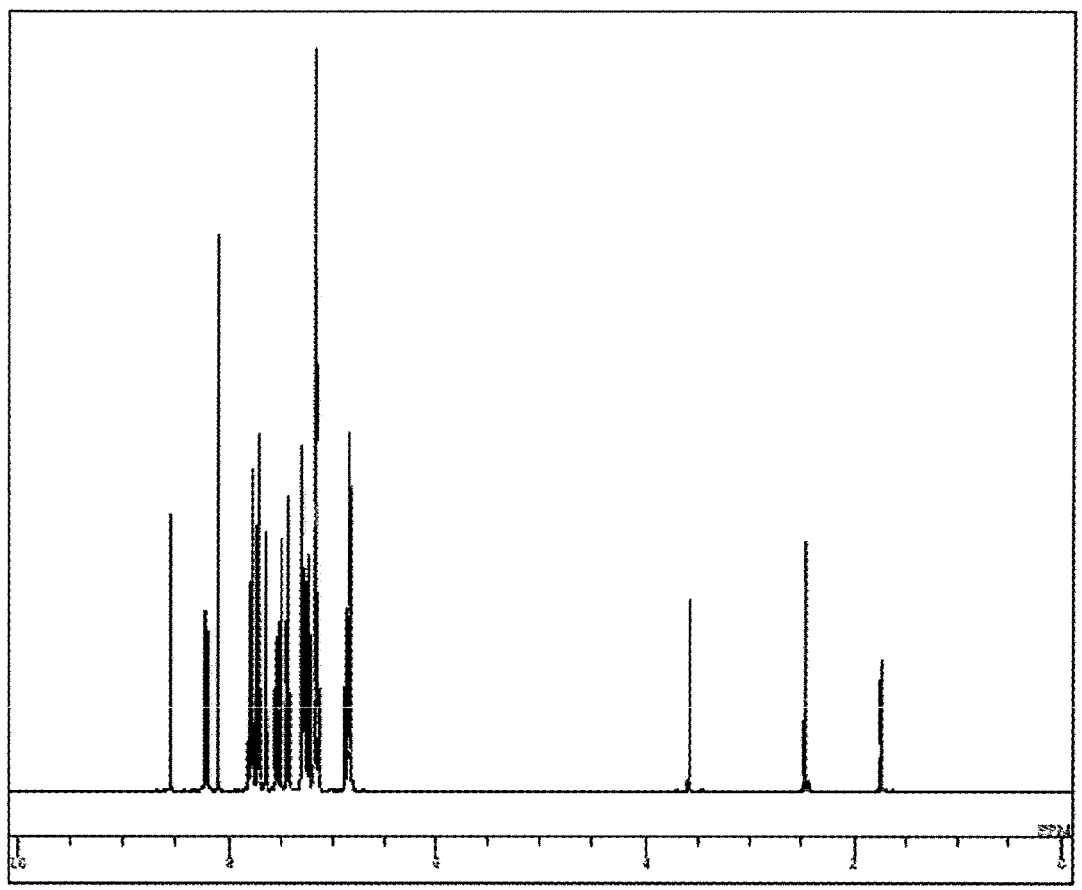
FIG. 1 is a $^1$H-NMR chart of a compound (compound 4) of Example 1 of the invention.

As shown above, the compound having the indolocarbazole ring structure of the invention is represented by the following general formula (1),

[Chemical 5]

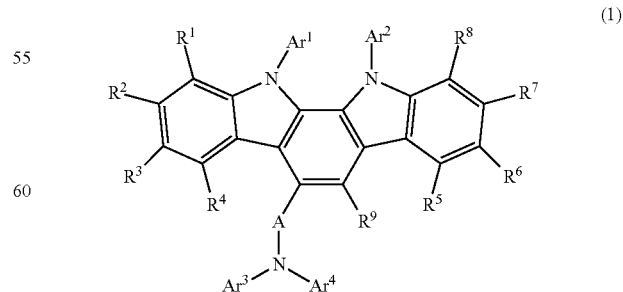

(1)

In the above general formula (1), the groups denoted by A, Ar$^1$ to Ar$^4$ and R$^1$ to R$^9$ are as described below.

(Group A)

In the general formula (1), the group A is an aromatic hydrocarbon group or an aromatic heterocyclic group. The aromatic hydrocarbon group and the aromatic heterocyclic group are not limited to those of the single ring but may be those having a multi-ring structure condensed with a hydrocarbon ring or with a hetero ring.

For instance, the aromatic hydrocarbon group is a divalent group as represented by phenylene group, biphenylene group, terphenylene group, tetrakisphenylene, naphthylene group, anthrylene group, phenanthrylene group, fluorenylene group or phenanthrolylene group.

The aromatic heterocyclic group, too, is a divalent group such as indenylene group, pyrenylene group, perylenylene group, fluoranthenylene group, triphenylenylene group, pyridinylene group, pyrimidinylene group, quinolylene group, isoquinolylene group, indolylene group, carbazolylene group, quinoxalylene group, benzoimidazolylene group, pyrazolylene group, naphthyridinylene group, phenanthrolynylene group, acrydinylene group, thienylene group, benzothienylene group, benzothiazolylene group and dibenzothienylene group.

The aromatic hydrocarbon group and the aromatic heterocyclic group denoted by A may, further, form a ring by being bonded with $Ar^3$ or $Ar^4$ that will be described later. In the general formula (1a) that will be described later, $Ar^4$ is bonded to the group A to form another ring.

Further, the aromatic hydrocarbon group and the aromatic heterocyclic group may have a substituent. As the substituent, there can be exemplified deuterium atom; cyano group; nitro group; halogen atoms such as fluorine atom, chlorine atom, bromine atom and iodine atom; straight chain or branched alkyl groups having 1 to 6 carbon atoms, such as methyl group, ethyl group, n-propyl group, isopropyl group, n-butyl group, isobutyl group, tert-butyl group, n-pentyl group, isopentyl group, neopentyl group and n-hexyl group; cycloalkyl groups having 5 to 10 carbon atoms, such as cyclopentyl group, cyclohexyl group, 1-adamantyl group and 2-adamantyl group; straight chain or branched alkoxy groups having 1 to 6 carbon atoms, such as methoxy group, ethoxy group and propyloxy group; cycloalkyloxy groups having 5 to 10 carbon atoms, such as cyclopentyloxy group, cyclohexyloxy group, cycloheptyloxy group, cyclooctyloxy group, 1-adamantyloxy group and 2-adamantyloxy group; straight chain or branched alkenyl groups having 2 to 6 carbon atoms, such as allyl group, isopropenyl group and 2-butenyl group; aryloxy groups such as phenoxy group and tolyloxy group; arylalkoxy groups such as benzyloxy group and phenetyloxy group; aromatic hydrocarbon groups or condensed polycyclic aromatic groups, such as phenyl group, biphenylyl group, terphenylyl group, naphthyl group, anthracenyl group, phenanthryl group, fluorenyl group, indenyl group, pyrenyl group, perylenyl group, fluoranthenyl group and triphenylenyl group; and aromatic heterocyclic groups such as pyridyl group, furanyl group, pyranyl group, thienyl group, furyl group, pyrolyl group, quinolyl group, isoquinolyl group, benzofuranyl group, benzothienyl group, indolyl group, carbazolyl group, benzoxazolyl group, benzothiazolyl group, quinoxalyl group, benzimidazolyl group, pyrazolyl group, dibenzofuranyl group, dibenzothienyl group and carbolynyl group.

The above substituents may, further, have a substituent. Further, the substituents may be simply bonded together or may be bonded together via a substituted or unsubstituted methylene group, oxygen atom or sulfur atom to form a ring.

($Ar^1$ to $Ar^4$)

$Ar^1$ to $Ar^4$, too, denote, respectively, aromatic hydrocarbon groups or aromatic heterocyclic groups which, however, are monovalent groups. These aromatic hydrocarbon groups and aromatic heterocyclic groups, too, may not be limited to those having a single ring but may be those having a multi-ring structure condensed with a hydrocarbon ring or a heterocyclic ring.

The monovalent aromatic hydrocarbon group can be represented by phenyl group, biphenylyl group, terphenylyl group, naphthyl group, anthryl group, phenanthryl group and fluorenyl group.

As the monovalent aromatic heterocyclic group, further, there can be exemplified indenyl group, pyrenyl group, perylenyl group, fluoranthenyl group, triphenylenyl group, pyridyl group, furanyl group, pyranyl group, thienyl group, quinolyl group, isoquinolyl group, benzofuranyl group, benzothienyl group, indolyl group, carbazolyl group, benzoxazolyl group, benzothiazolyl group, quinoxalyl group, benzimidazolyl group, pyrazolyl group, dibenzofuranyl group, dibenzothienyl group and carbolynyl group. In these heterocyclic groups, it is desired that not the hetero atom but the carbon atom in the ring is bonded to the N atom in the general formula (1) from the standpoint of stability and heat resistance of the compound.

Moreover, the monovalent aromatic hydrocarbon group and the monovalent aromatic heterocyclic group, too, may have a substituent. The substituent may be the same substituent as the one possessed by the group A.

Further, $Ar^3$ and $Ar^4$ may be simply bonded together, or may be bonded together or may be bonded to the above group A via a substituted or unsubstituted methylene group, oxygen atom or sulfur atom to form another ring.

($R^1$ to $R^9$)

$R^1$ to $R^9$ are, respectively, hydrogen atoms, deuterium atoms, fluorine atoms, chlorine atoms, cyano groups, nitro groups, alkyl groups having 1 to 6 carbon atoms, cycloalkyl groups having 5 to 10 carbon atoms, alkenyl groups having 2 to 6 carbon group, alkyloxy groups having 1 to 6 carbon atoms, cycloalkyloxy groups having 5 to 10 carbon atoms, monovalent aromatic hydrocarbon groups, monovalent aromatic heterocyclic groups or aryloxy groups.

The alkyl group having 1 to 6 carbon atoms may be of the form of a straight chain or of the branched form, and may be methyl group, ethyl group, n-propyl group, isopropyl group, n-butyl group, isobutyl group, tert-butyl group, n-pentyl group, isopentyl group, neopentyl group or n-hexyl group.

As the cycloalkyl group having 5 to 10 carbon atoms, there can be exemplified cyclopentyl group, cyclohexyl group, 1-adamantyl group and 2-adamantyl group.

The alkenyl group having 2 to 6 carbon atoms may be of the form of a straight chain or of the branched form, and its concrete examples include vinyl group, aryl group, isopropenyl group and 2-butenyl group.

The alkyloxy group having 1 to 6 carbon atoms, too, may be of the form of a straight chain or of the branched form, and its concrete examples include methyloxy group, ethyloxy group, n-propyloxy group, isopropyloxy group, n-butyloxy group, tert-butyloxy group, n-pentyloxy group and n-hexyloxy group.

Examples of the cycloalkyloxy group having 5 to 10 carbon atoms include cyclopentyloxy group, cyclohexyloxy group, cycloheptyloxy group, cyclooctyloxy group, 1-adamantyloxy group and 2-adamantyloxy group.

The monovalent aromatic hydrocarbon groups and aromatic heterocyclic groups, too, may not be limited to those having a single ring but may be those having a multi-ring structure condensed with a hydrocarbon ring or a heterocyclic ring as described with reference to the groups $Ar^1$ to $Ar^4$.

As the aromatic hydrocarbon group, there can be exemplified phenyl group, biphenyl group, terphenylyl group, naphthyl group, anthryl group, phenanthryl group, fluorenyl group, indenyl group, pyrenyl group, perylenyl group, fluoranthenyl group and triphenylenyl group.

As the aromatic heterocyclic group, there can be exemplified pyridyl group, furanyl group, pyranyl group, thienyl group, quinolyl group, isoquinolyl group, benzofuranyl group, benzothienyl group, indolyl group, carbazolyl group, benzoxazolyl group, benzothiazolyl group, quinoxalyl group, benzimidazolyl group, pyrazolyl group, dibenzofuranyl group, dibenzothienyl group and carbolinyl group. In these heterocyclic groups, further, it is desired that not the hetero atom but the carbon atom in the ring is bonded to the carbon atom in the aromatic ring of the general formula (1) from the standpoint of stability and heat resistance of the compound.

As the aryloxy group, there can be exemplified phenoxy group, biphenylyloxy group, terphenylyloxy group, naphthyloxy group, anthryloxy group, phenanthryloxy group, fluorenyloxy group, indenyloxy group, pyrenyloxy group and perylenyloxy group.

Of the groups denoted by $R^1$ to $R^9$, any of alkyl group, cycloalkyl group, alkenyl group, alkyloxy group, cycloalkyloxy group, aromatic hydrocarbon group, aromatic heterocyclic group and aryloxy group may possess substituents. The substituents are the same substituents as those which may be possessed by the group A or by the groups $Ar^1$ to $Ar^4$ provided the numbers of carbon atoms of the groups are within predetermined ranges. These substituents may, further, possess a substituent. Further, these substituents may be simply bonded together or may be bonded together via a substituted or unsubstituted methylene group, oxygen atom or sulfur atom to form another ring.

Further, the above $R^1$ to $R^9$ may possess a di-substituted amino group as the substituent in addition to possessing the above-mentioned substituents. As the substituent possessed by the di-substituted amino group (i.e., as the group bonded to the N atom of the amino group), there can be exemplified alkyl group, aromatic hydrocarbon group, condensed polycyclic aromatic group, aralkyl group, aromatic heterocyclic group and alkenyl group. Specifically, diphenylamino group, dinaphthylamino group and phenylnaphthylamino group are preferred as the di-substituted amino groups.

In the invention, of the above-mentioned $R^1$ to $R^9$, the group $R^9$ is, desirably, an aromatic hydrocarbon group having a single ring or a multiplicity of rings, and is, particularly desirably, a phenyl group, biphenyl group or naphthyl group.

The aromatic hydrocarbon group that is desired as the group $R^9$ may have a substitutent and, specifically, may have the above-mentioned diphenylamino group, dinaphthylamino group or phenylnaphthylamino group as the substituent.

Of the compounds having the indolocabazole ring structure of the invention represented by the above general formula (1), a compound represented by the following general formula (1a) is specifically preferred from the standpoint of heat resistance and stability.

[Chemical 6]

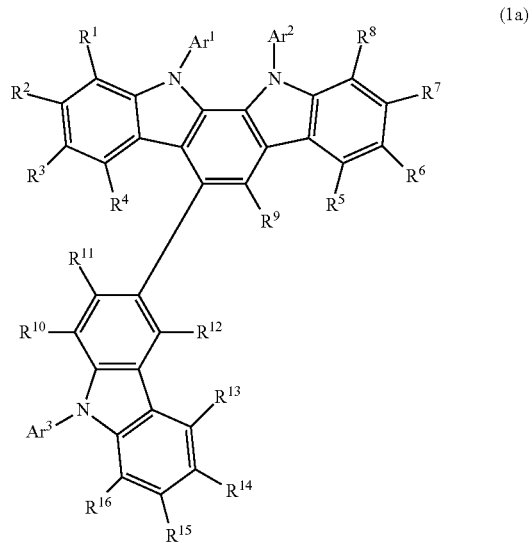

(1a)

In the above general formula (1a), $Ar^1$ to $Ar^3$ and $R^1$ to $R^9$ are as defined in the above general formula (1).

Further, $R^{10}$ to $R^{16}$ are, respectively, hydrogen atoms, deuterium atoms, fluorine atoms, chlorine atoms, cyano groups, nitro groups, alkyl groups having 1 to 6 carbon atoms, cycloalkyl groups having 5 to 10 carbon atoms, alkenyl groups having 2 to 6 carbon group, alkyloxy groups having 1 to 6 carbon atoms, cycloalkyloxy groups having 5 to 10 carbon atoms, aromatic hydrocarbon groups, aromatic heterocyclic groups or aryloxy groups. Among them, the alkyl groups, cycloalkyl groups, alkenyl groups, alkyloxy groups, aromatic hydrocarbon groups, aromatic heterocyclic groups and aryloxy groups may be the same groups as those exemplified above.

As described already, the compound of the general formula (1a) is the one in which the group A of the general formula (1) is a phenylene group, and the group $Ar^4$ is bonded to the phenylene group (single bond) to form a ring.

(Preparation of a Compound Having the Indolocarbazole Ring Structure)

The compound having the indolocarbazole ring structure of the invention mentioned above is a novel compound and can be synthesized as described below.

As the starting material, use is made of a 11,12-dihydroindolo[2,3-a]carbazole. The starting carbazole can be synthesized by, for example, reacting a 2-aminocyclohexanone hydrochloride with a phenylhydrazine hydrochloride (see Synlett., 1, 42 (2005)).

A 11,12-diphenyl-indolo[2,3-a]carbazole can be synthesized by subjecting the above starting carbazole and an iodobenzene to the condensation reaction such as Ullmann reaction.

The thus obtained 11,12-diphenyl-indolo[2,3-a]carbazole is turned into a bromo-form with an imide N-bromosuccinate to synthesize a 5-bromo-11,12-diphenyl-indolo[2,3-a] carbazole.

In synthesizing the bromo-substituted carbazole in a manner as described above, if there is used a 2-aminocyclohexanone hydrochloride substituted with a corresponding substituent, iodine or bromoaryl compound depending, for example, upon the structure of the general formula (1), then there can be synthesized a 5-bromo-substituted product of the 11,12-diaryl-indolo[2,3-a]carbazole that corresponds to the structure of the general formula (1).

Next, there is provided a boronic acid or a boronic ester synthesized by the reaction of an aryl halide substituted with various diarylamino groups with a pinacol borane or a bis(pinacolato)diboron (see, for example, J. Org. Chem., 60, 7508 (1995)).

By subjecting the boronic acid or the boronic ester and the 5-bromo-substituted product of the 11,12-diaryl-indolo[2,3-a]carbazole corresponding to the structure of the general formula (1) to the cross-coupling reaction such as the Suzuki coupling (see, for example, Synth. Commun., 11, 513 (1981)), there can be synthesized a compound having the desired indolocarbazole ring structure of the present invention.

The compound of the invention synthesized as described above can be purified by using a column chromatography, by using an adsorbent such as silica gel, activated carbon or activated clay, or by the recrystallization by using a solvent or by the crystallization method.

Among the compounds having the indolocarbazole ring structure represented by the general formula (1) of the invention, particularly desired compounds are as shown below concretely. Among the compounds shown below, the compounds represented by the above general formula (1a) are particularly preferred.

[Chemical 7]

(Compound 2)

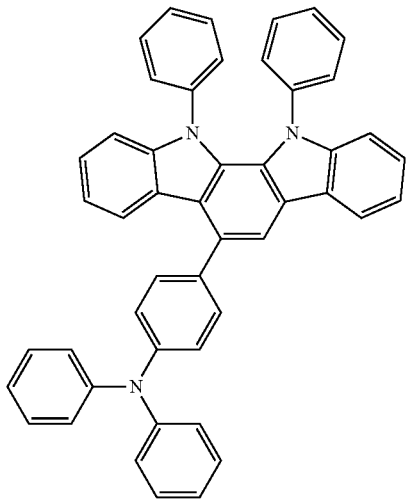

[Chemical 8]

(Compound 3)

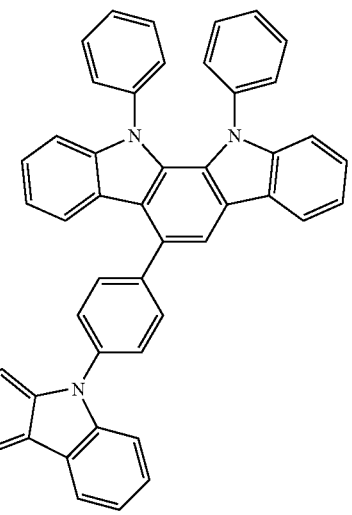

[Chemical 9]

(Compound 4)

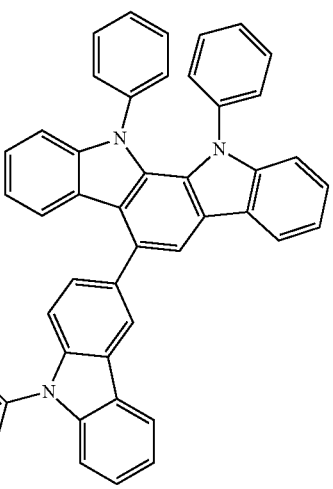

[Chemical 10]

(Compound 5)

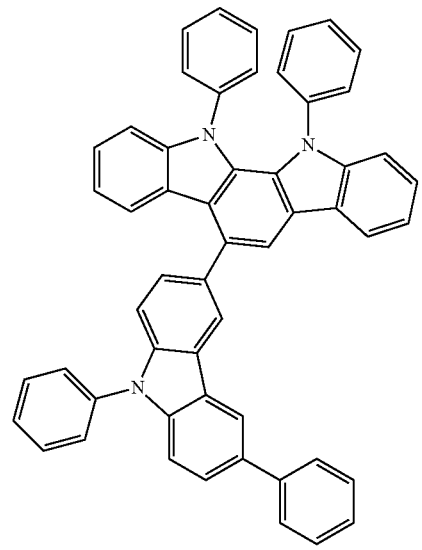

[Chemical 11]
(Compound 6)
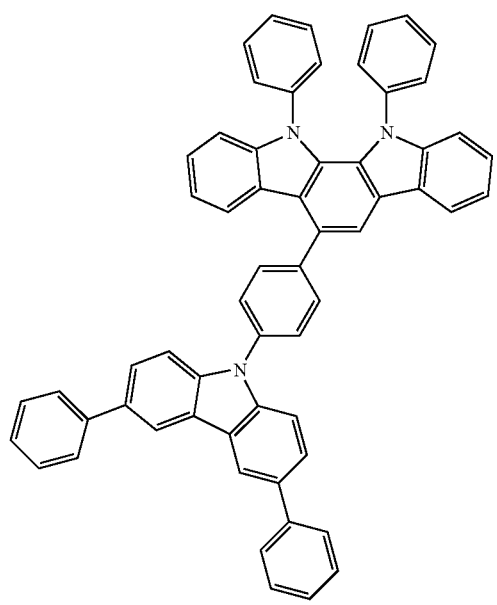
[Chemical 12]
(Compound 7)
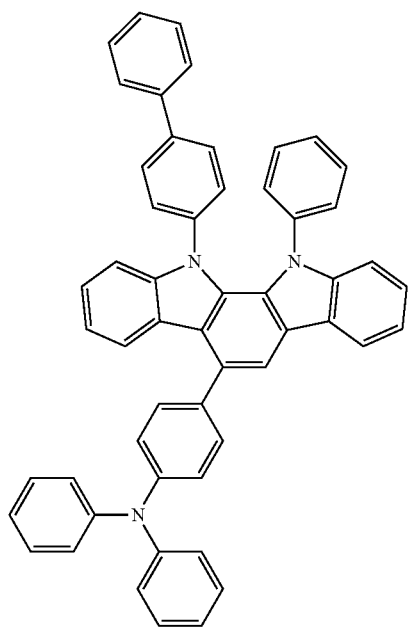
[Chemical 13]
(Compound 8)
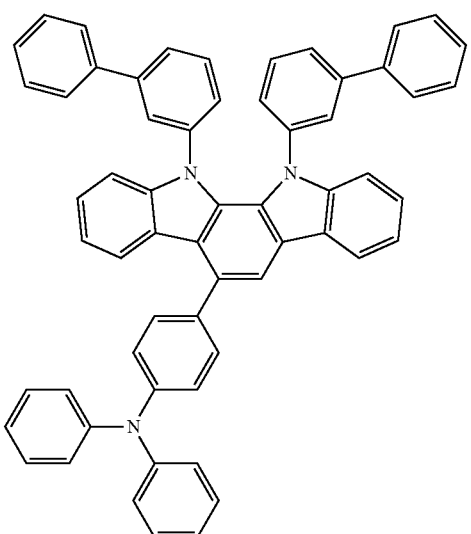
[Chemical 14]
(Compound 9)
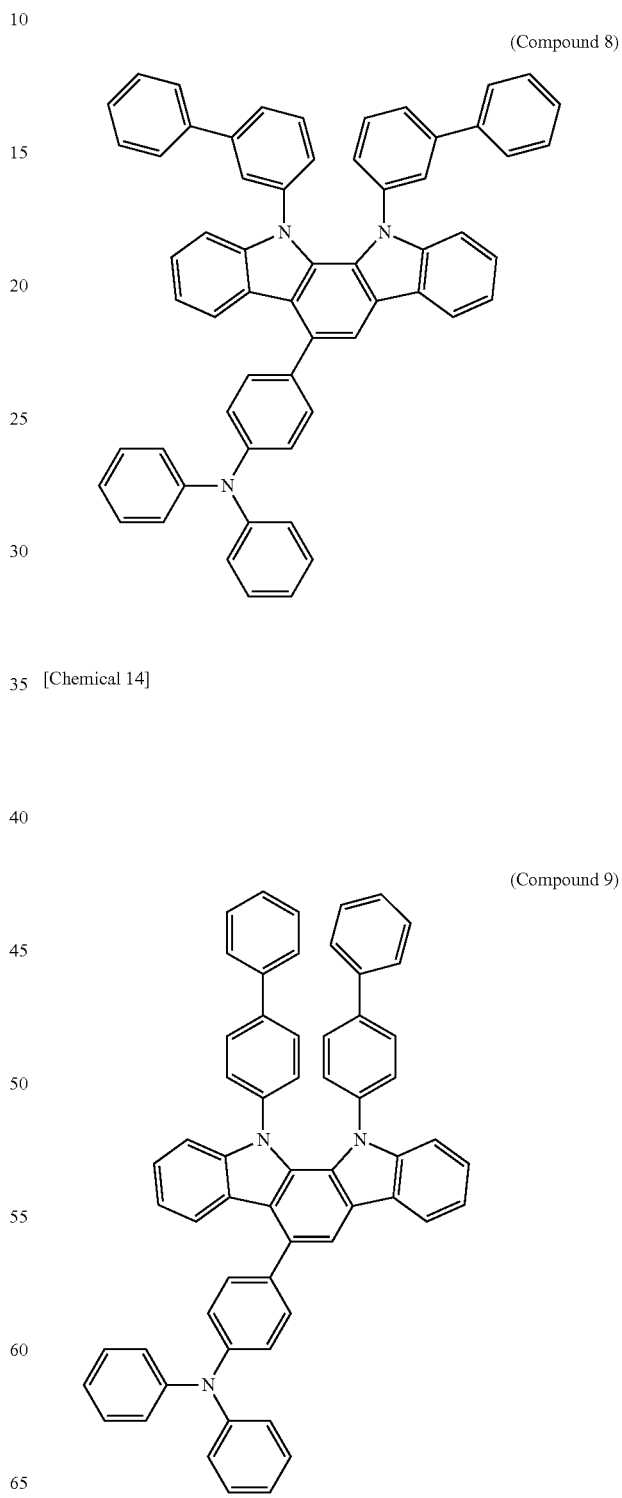

[Chemical 15]
(Compound 10)
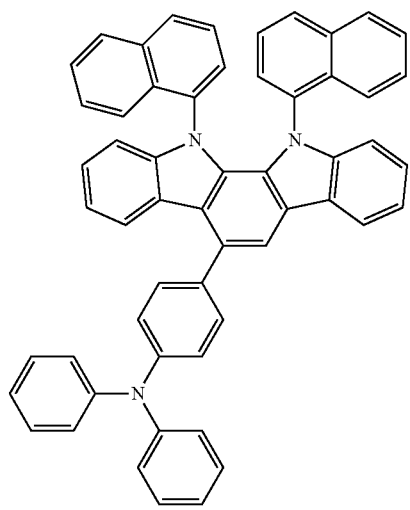
[Chemical 16]
(Compound 11)
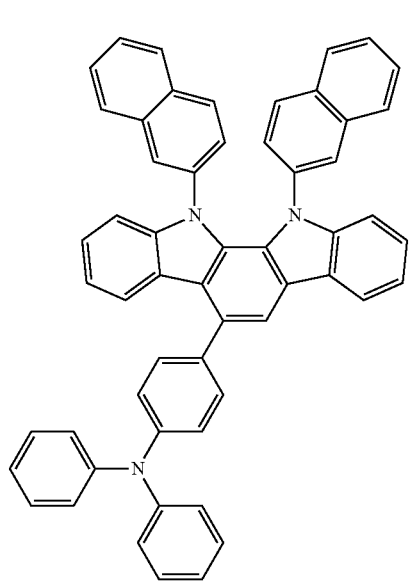
[Chemical 17]
(Compound 12)
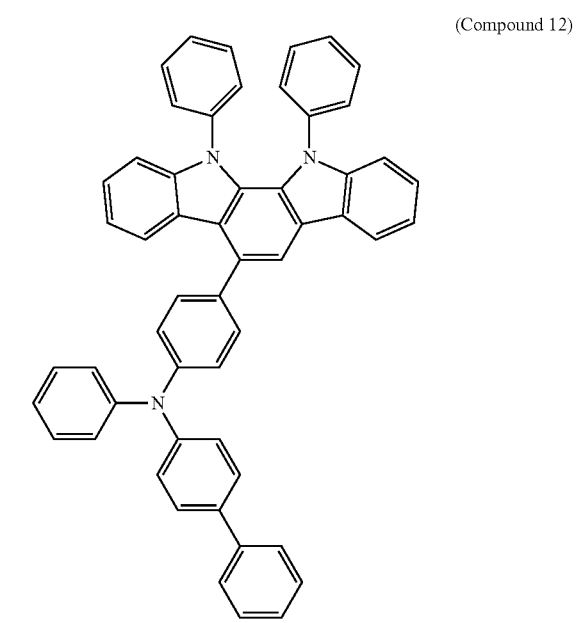
[Chemical 18]
(Compound 13)
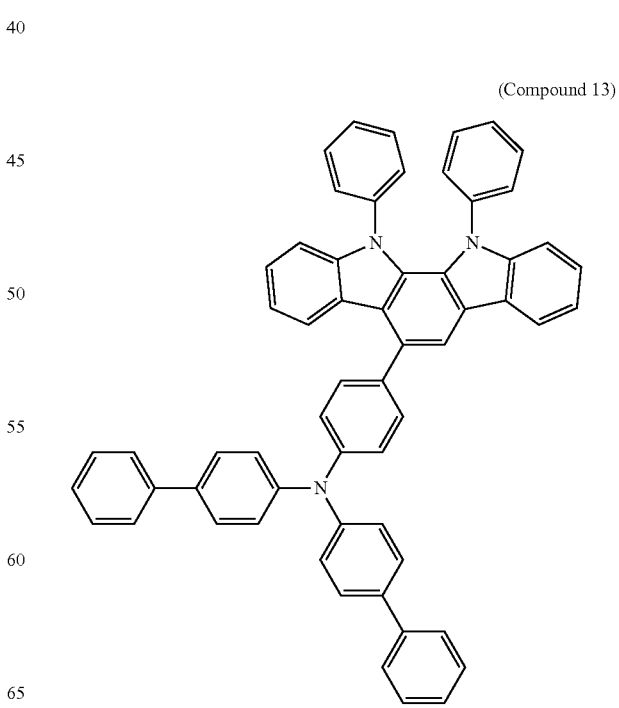

[Chemical 19]
(Compound 14)
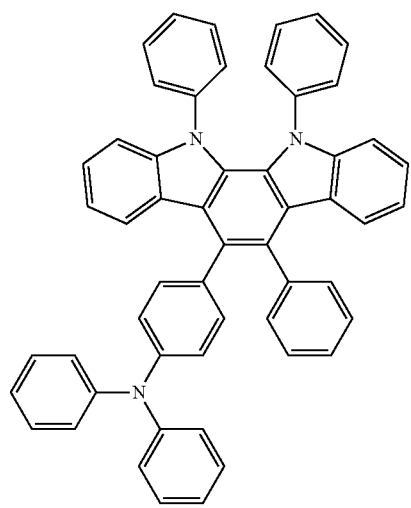
[Chemical 20]
(Compound 15)
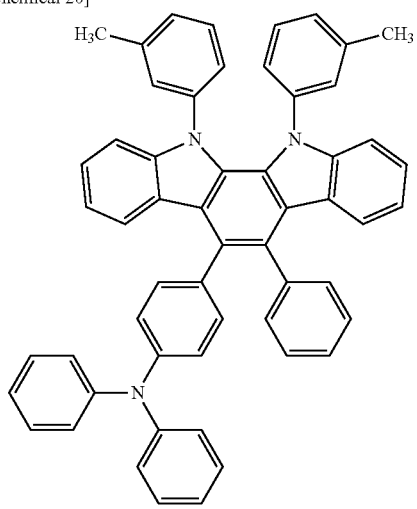
[Chemical 21]
(Compound 16)
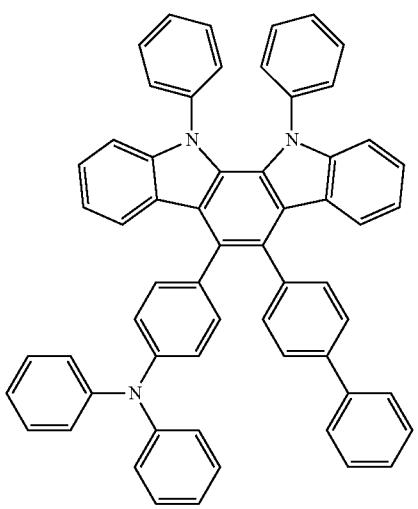
[Chemical 22]
(Compound 17)
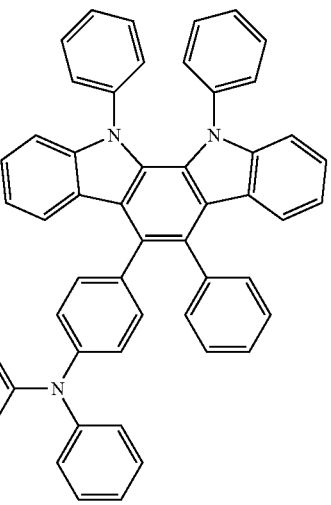
[Chemical 23]
(Compound 18)
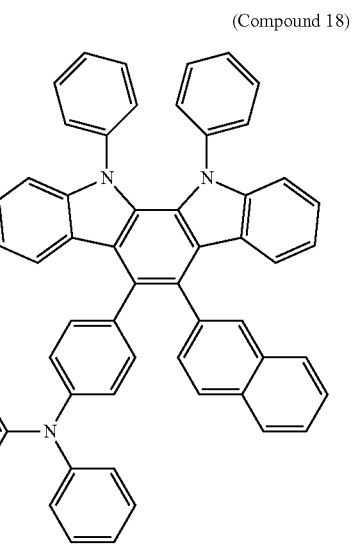
[Chemical 24]
(Compound 19)
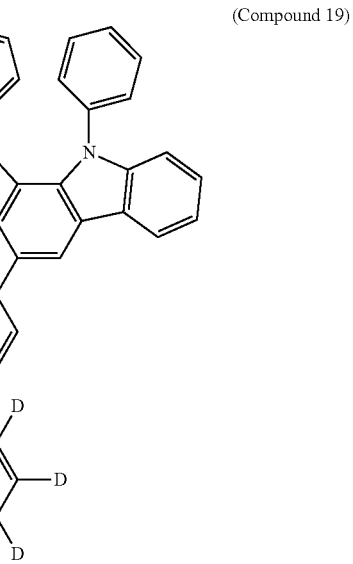

-continued
[Chemical 25] (Compound 20)
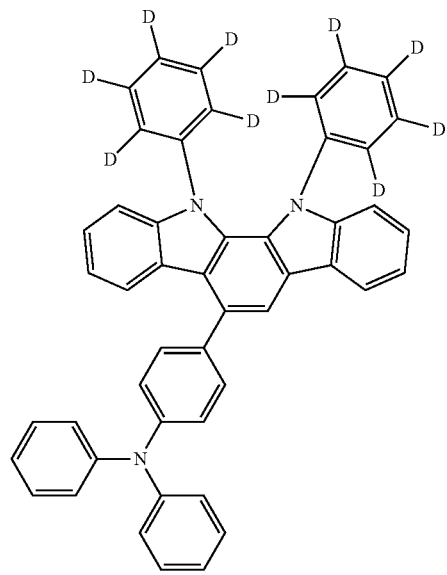
[Chemical 26] (Compound 21)
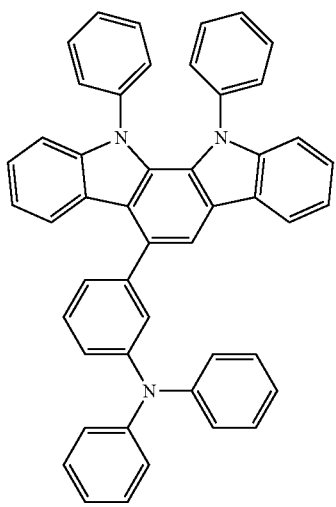
[Chemical 27] (Compound 22)
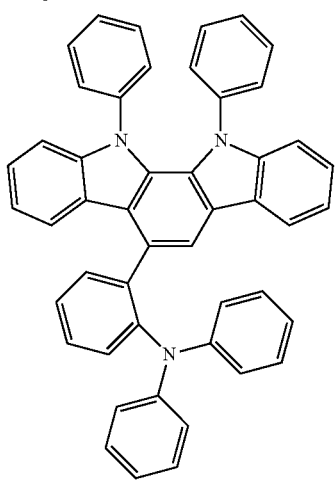
[Chemical 28] (Compound 23)
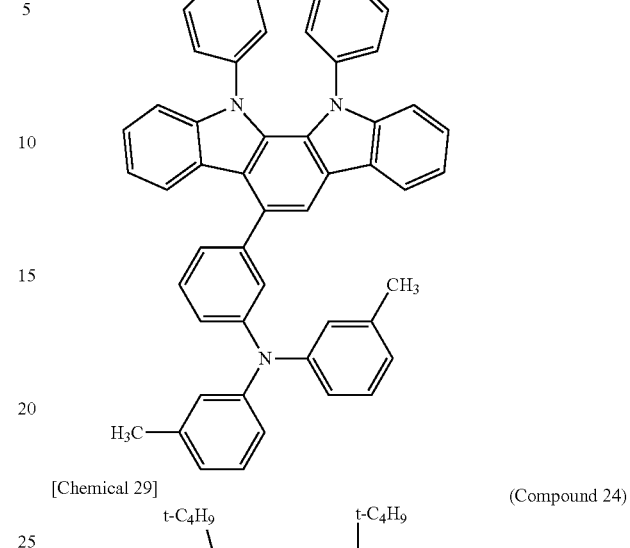
[Chemical 29] (Compound 24)
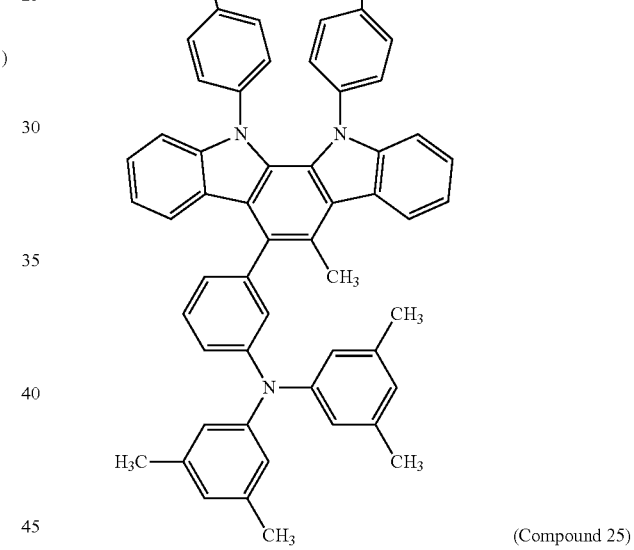
[Chemical 30] (Compound 25)
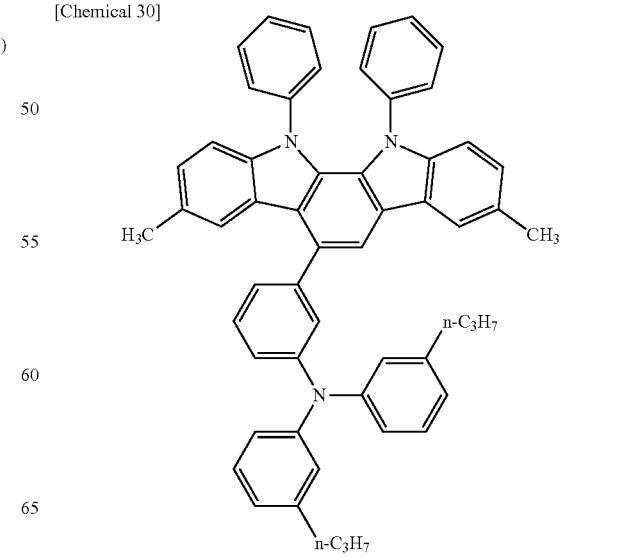

[Chemical 31]
(Compound 26)
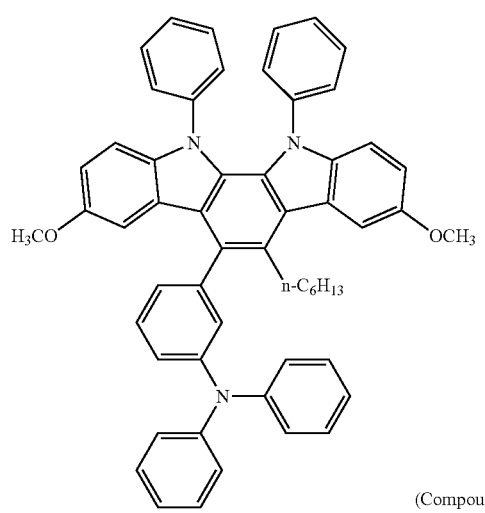
[Chemical 32]
(Compound 27)
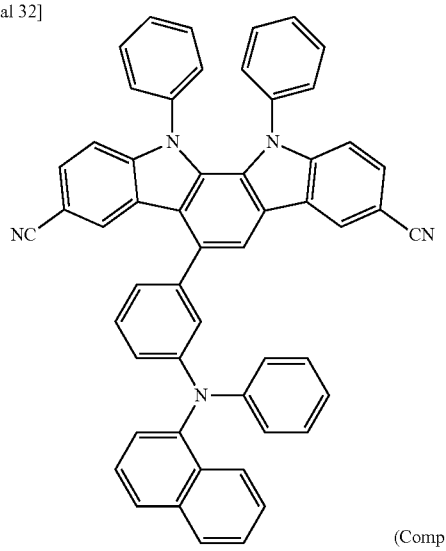
[Chemical 33]
(Compound 28)
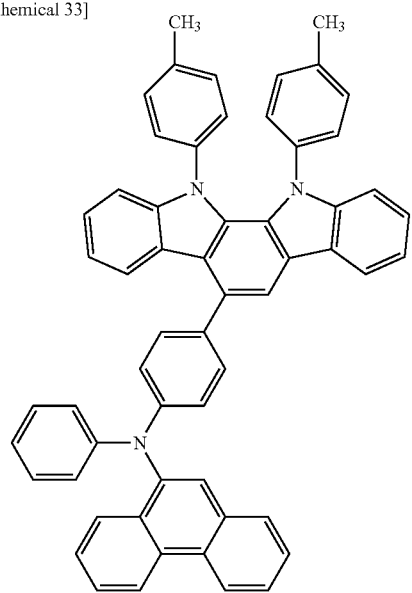
[Chemical 34]
(Compound 29)
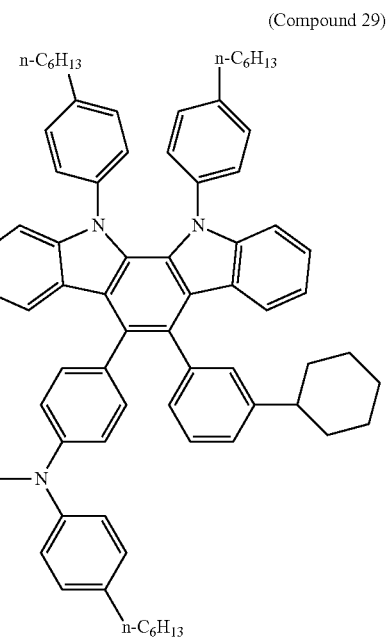
[Chemical 35]
(Compound 30)
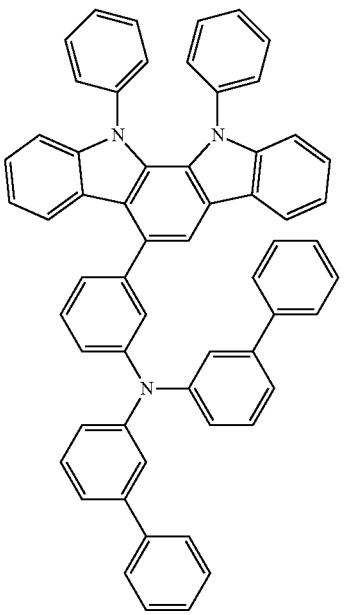

[Chemical 36]
(Compound 31)
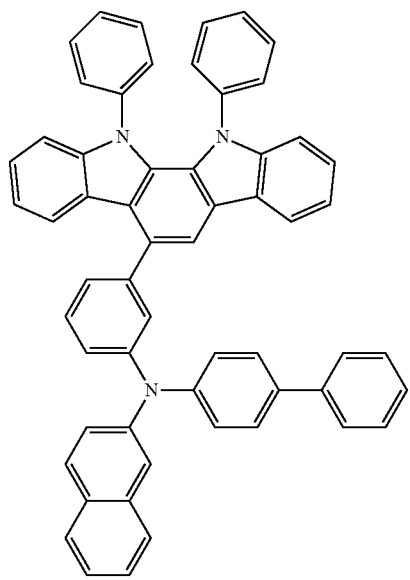
[Chemical 37]
(Compound 32)
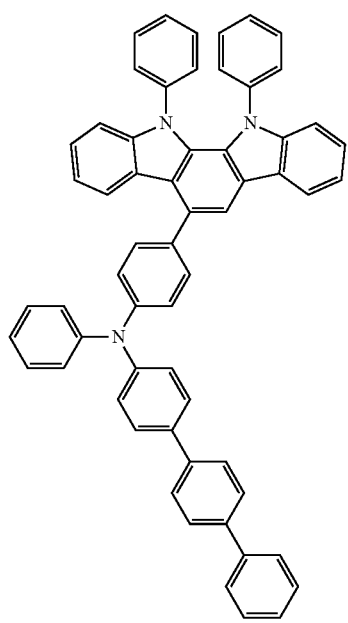
[Chemical 38]
(Compound 33)
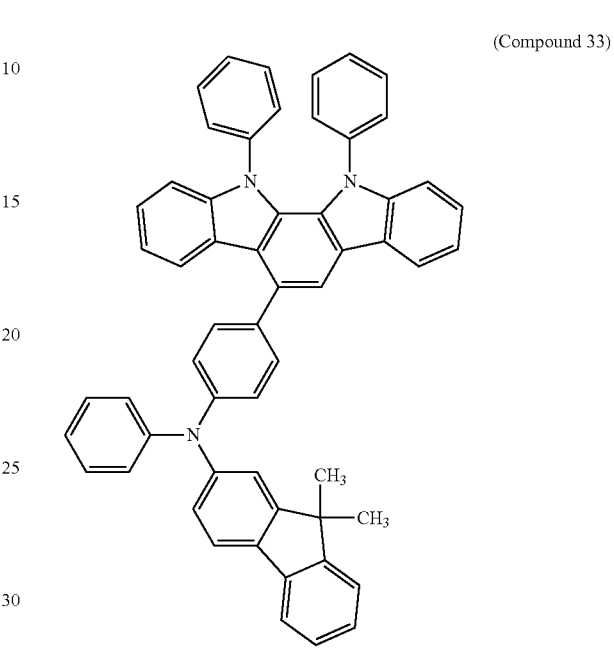
[Chemical 39]
(Compound 34)
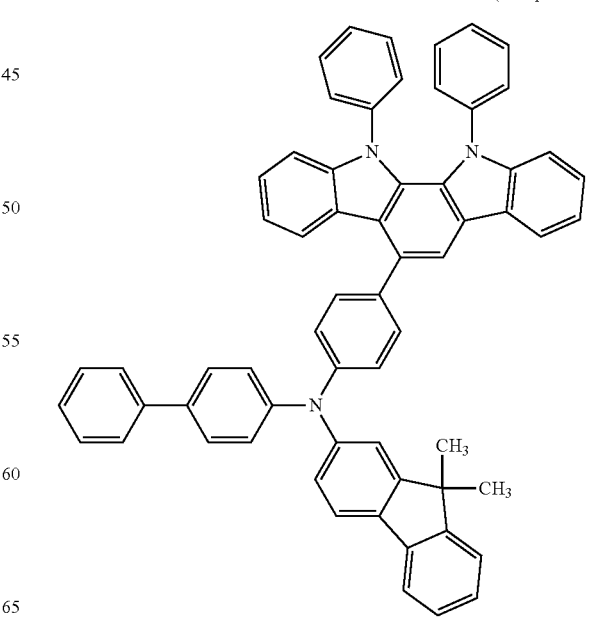

[Chemical 40]
(Compound 35)
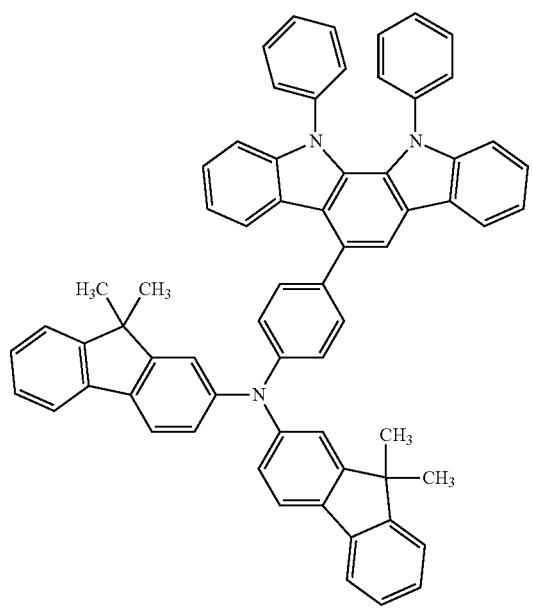
[Chemical 41]
(Compound 36)
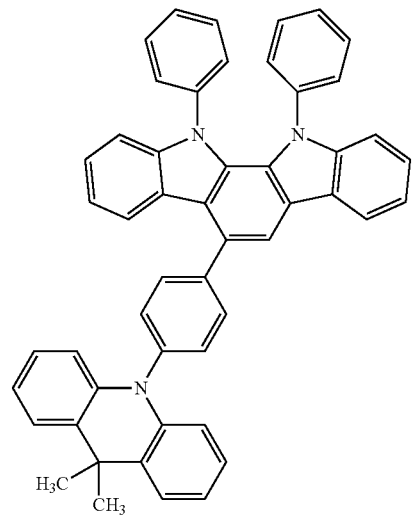
[Chemical 42]
(Compound 37)
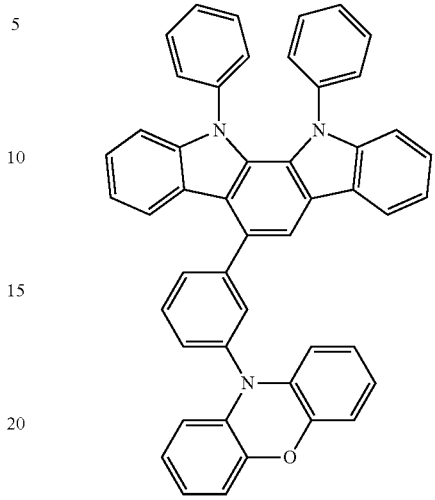
[Chemical 43]
(Compound 38)
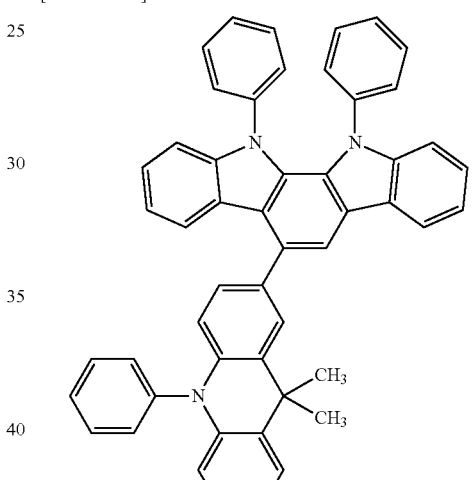
[Chemical 44]
(Compound 39)
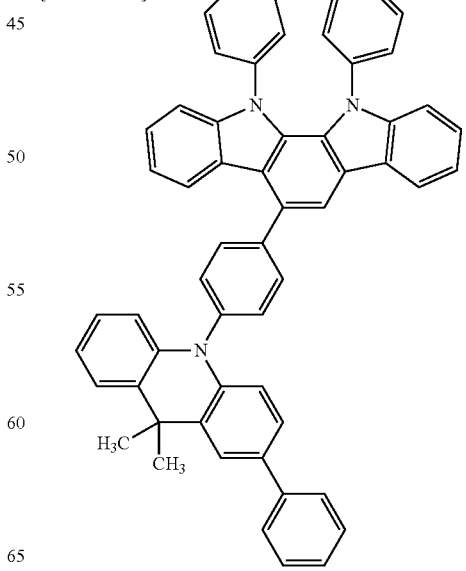

[Chemical 45]
(Compound 40)
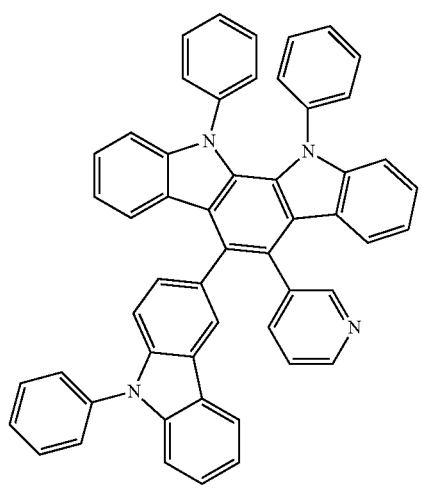
[Chemical 46]
(Compound 41)
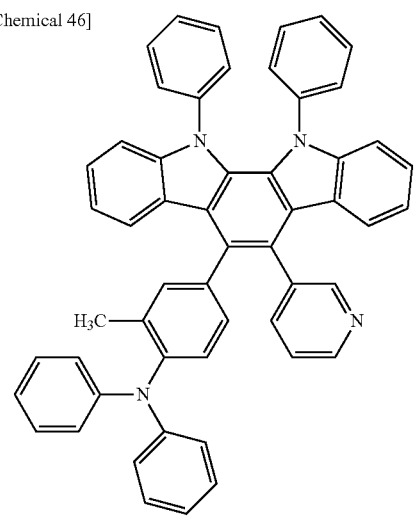
[Chemical 47]
(Compound 42)
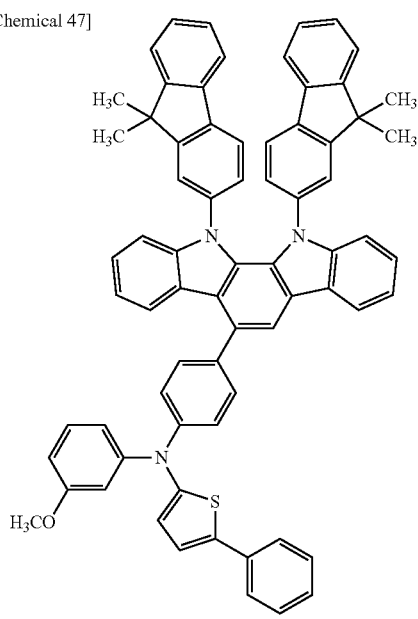
[Chemical 48]
(Compound 43)
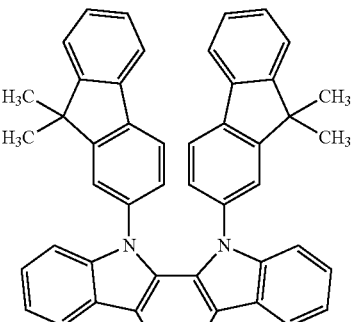
[Chemical 49]
(Compound 44)
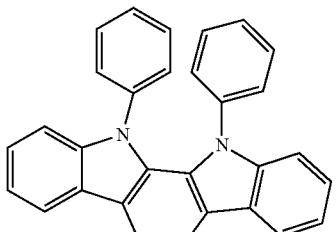
[Chemical 50]
(Compound 45)
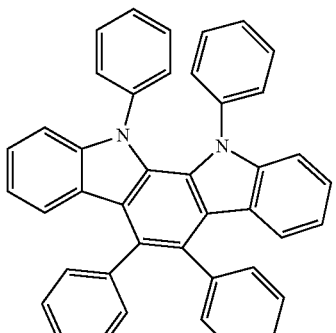

[Chemical 51]
(Compound 46)
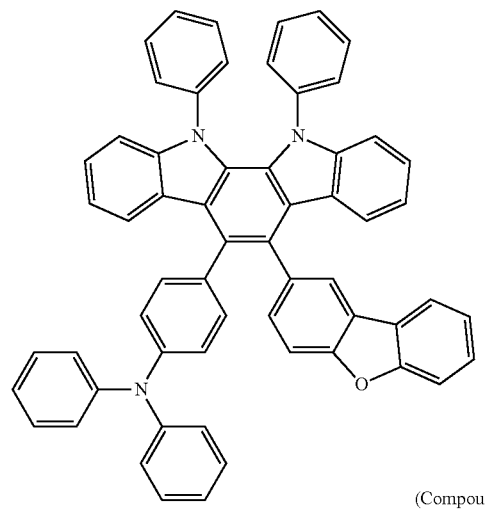
[Chemical 52]
(Compound 47)
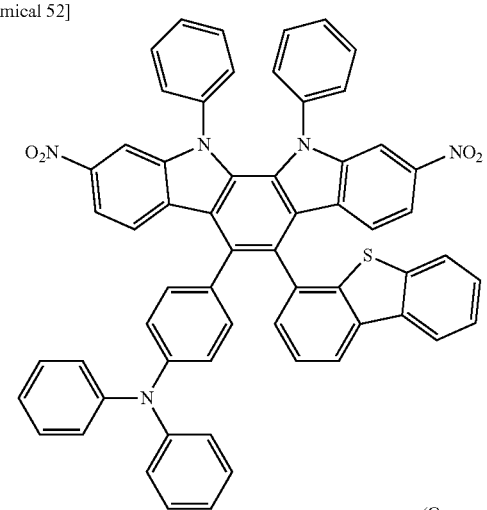
[Chemical 53]
(Compound 48)
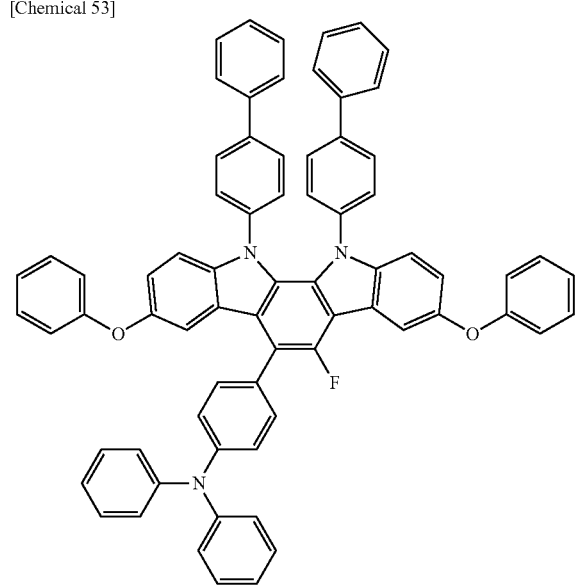
[Chemical 54]
(Compound 49)
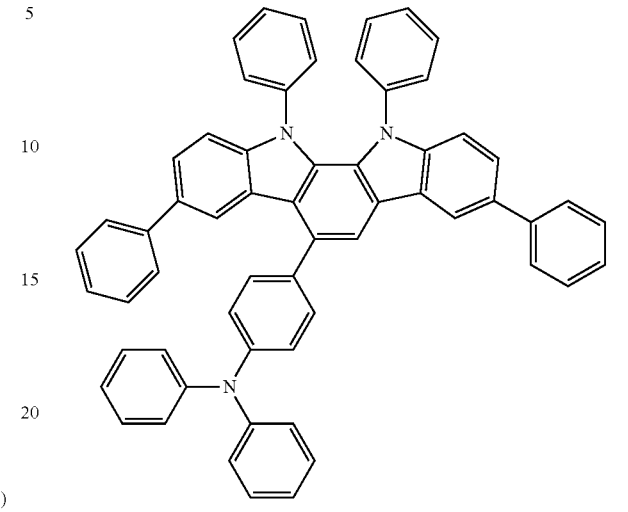
[Chemical 55]
(Compound 50)
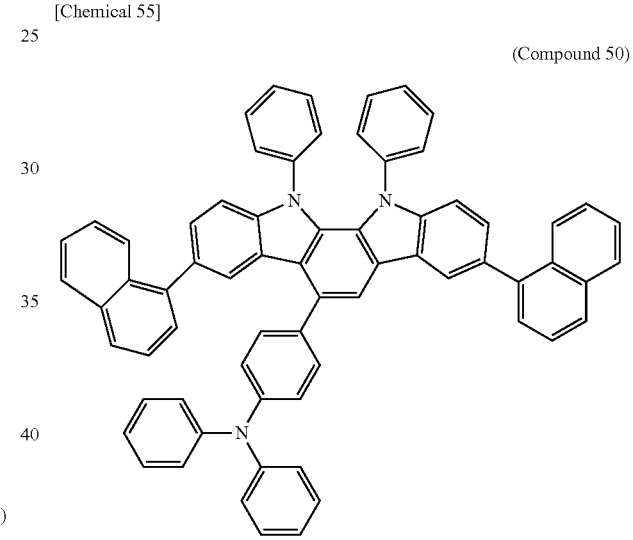
[Chemical 56]
(Compound 51)
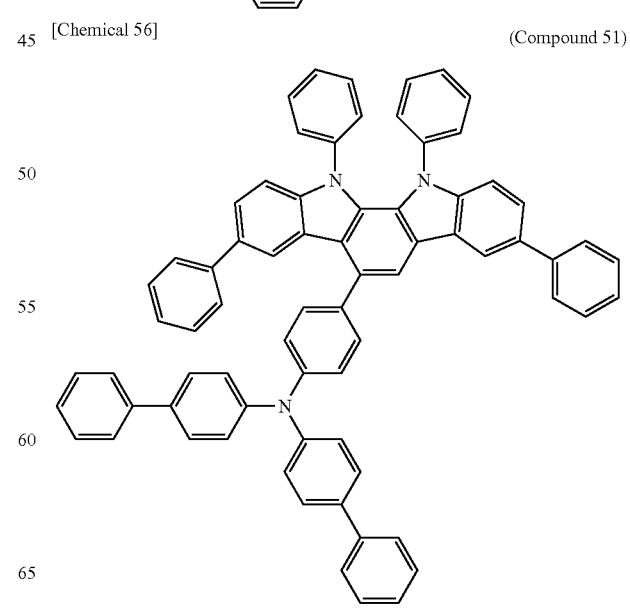

-continued
[Chemical 57]
(Compound 52)
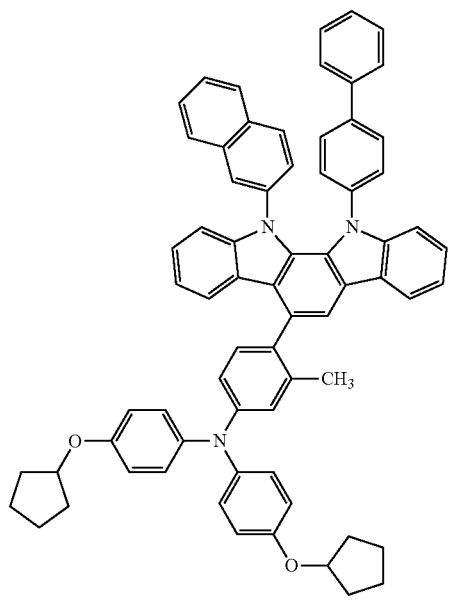
[Chemical 58]
(Compound 53)
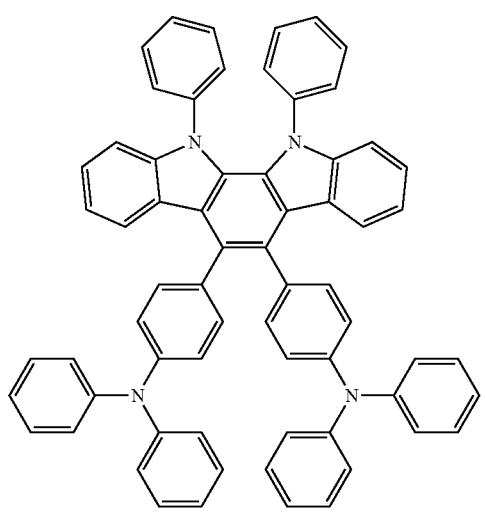
[Chemical 59]
(Compound 54)
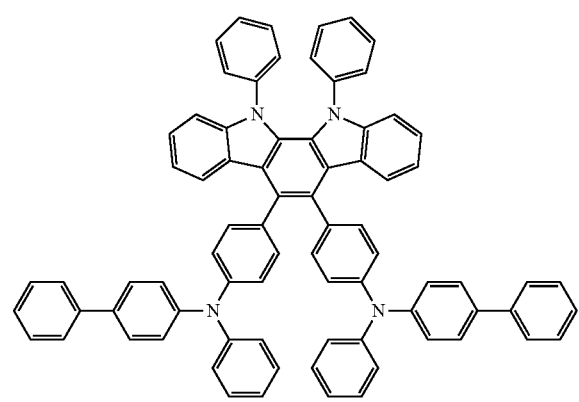
-continued
[Chemical 60]
(Compound 55)
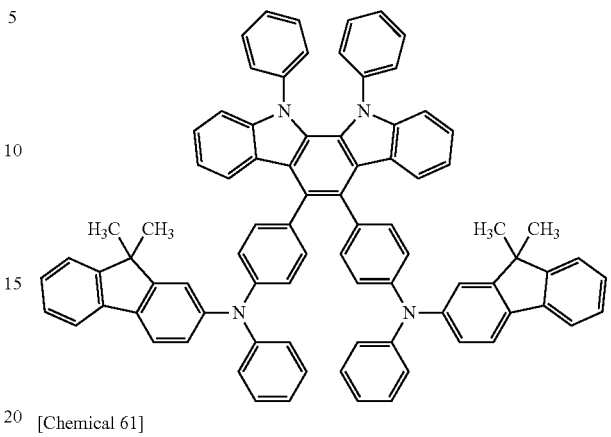
[Chemical 61]
(Compound 56)
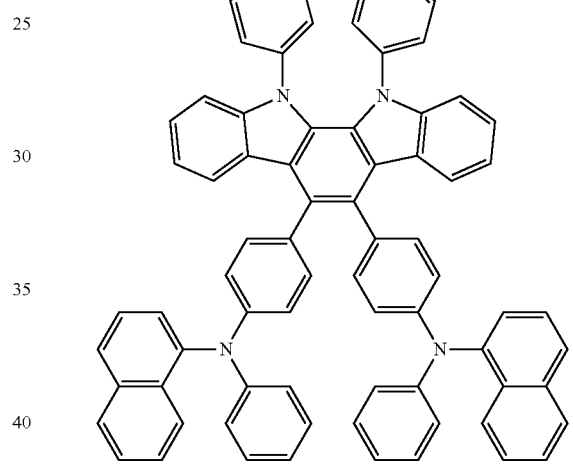
[Chemical 62]
(Compound 57)
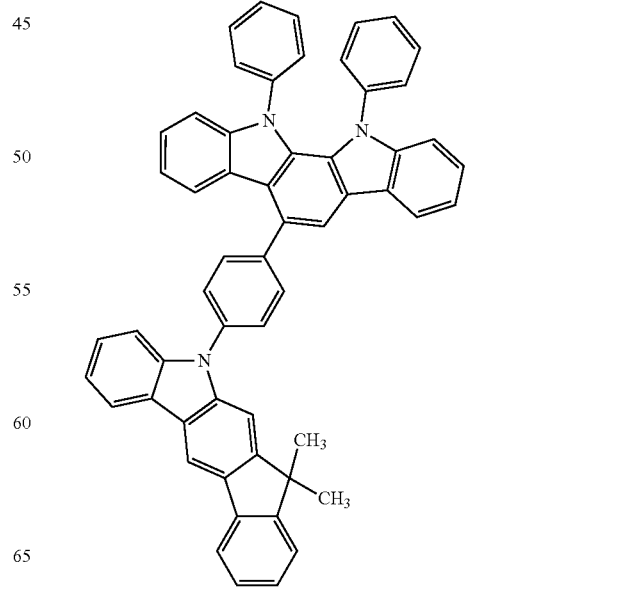

[Chemical 63]
(Compound 58)
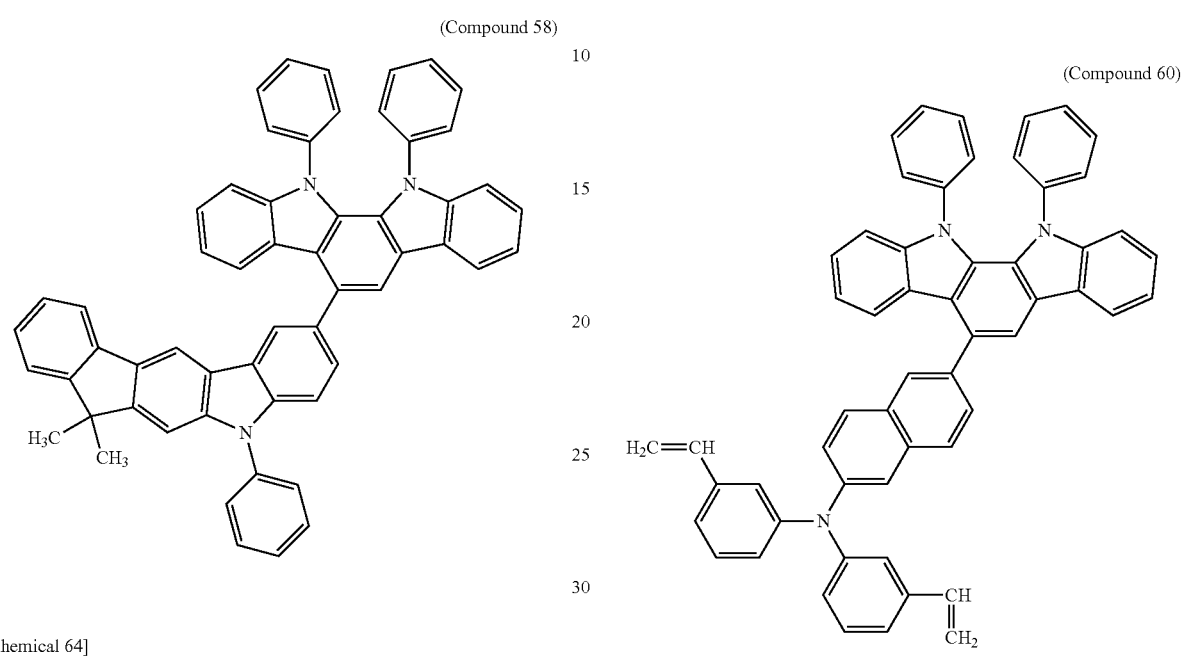
[Chemical 64]
(Compound 59)
[Chemical 65]
(Compound 60)
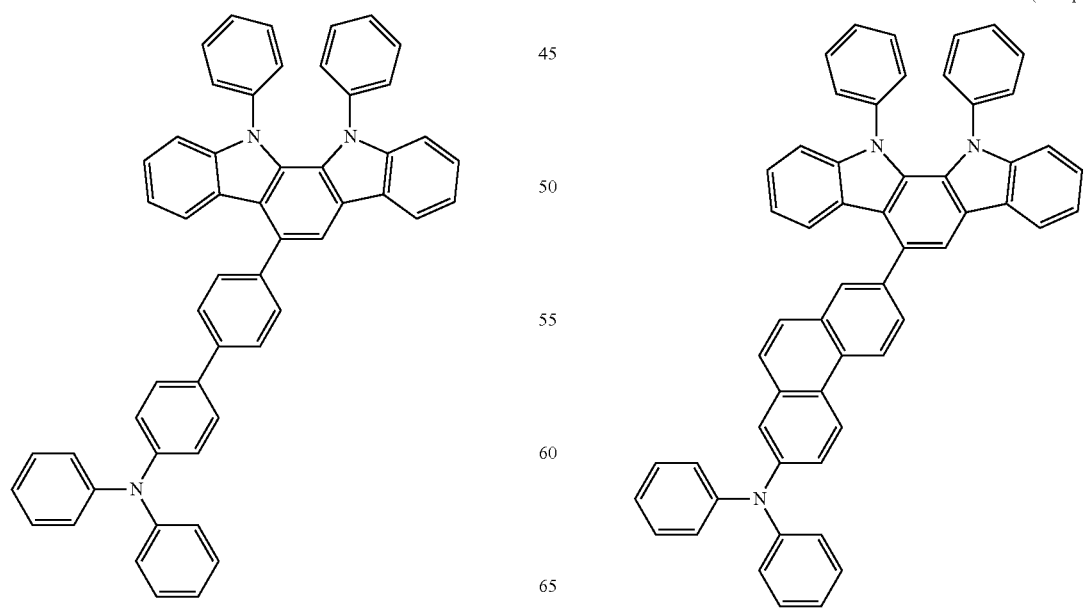
[Chemical 66]
(Compound 61)

[Chemical 67]
(Compound 62)
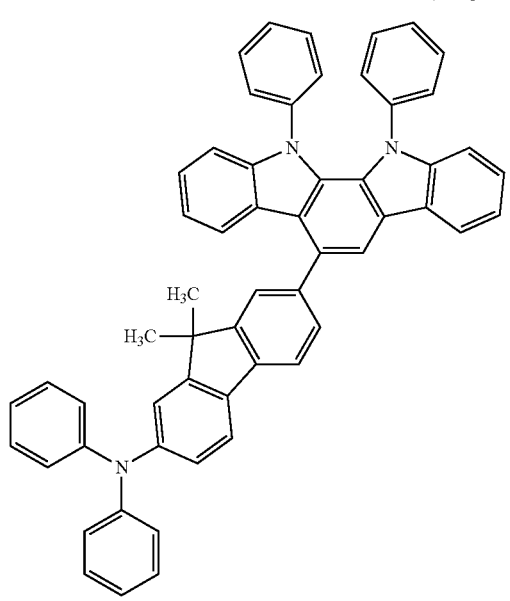
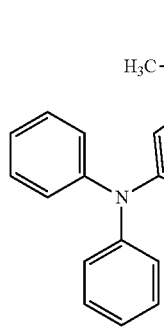
[Chemical 68]
(Compound 63)
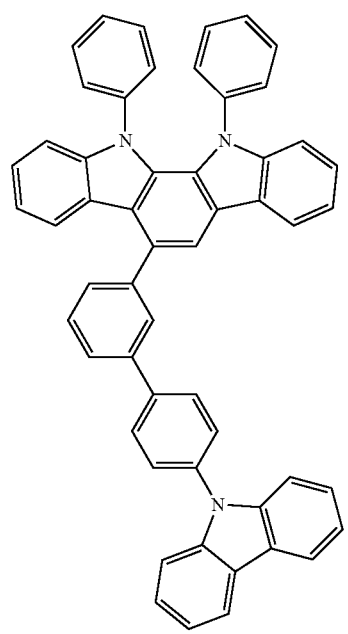
[Chemical 69]
(Compound 64)
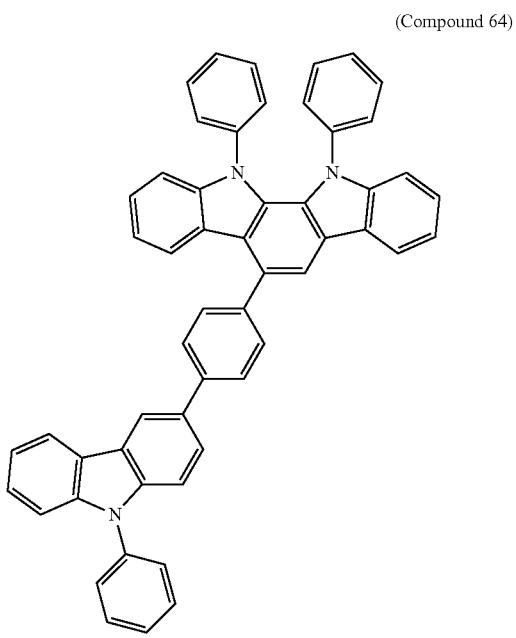
[Chemical 70]
(Compound 65)
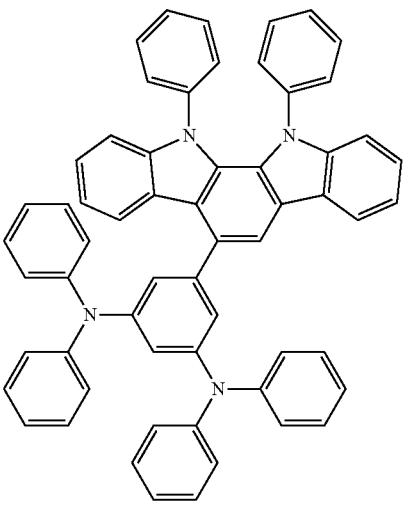

[Chemical 71]
(Compound 66)
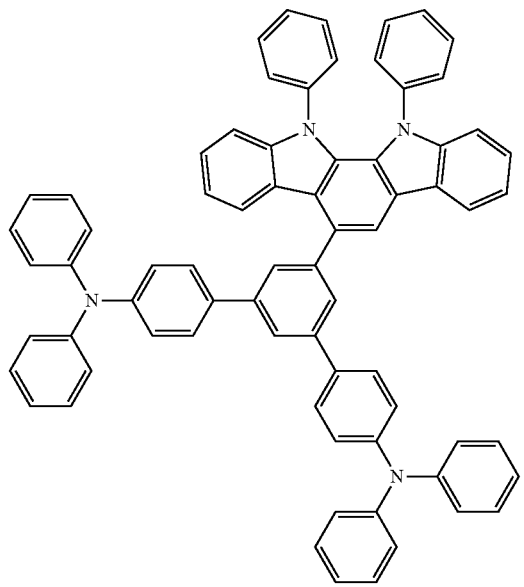
[Chemical 72]
(Compound 67)
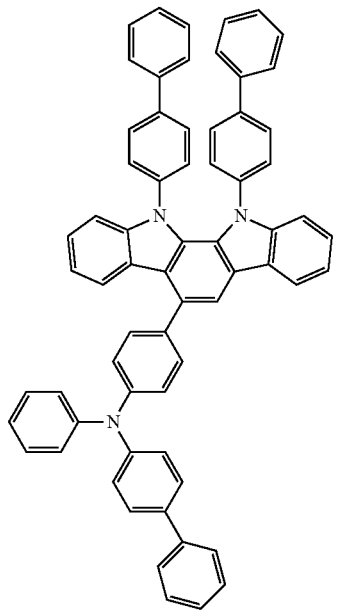
[Chemical 73]
(Compound 68)
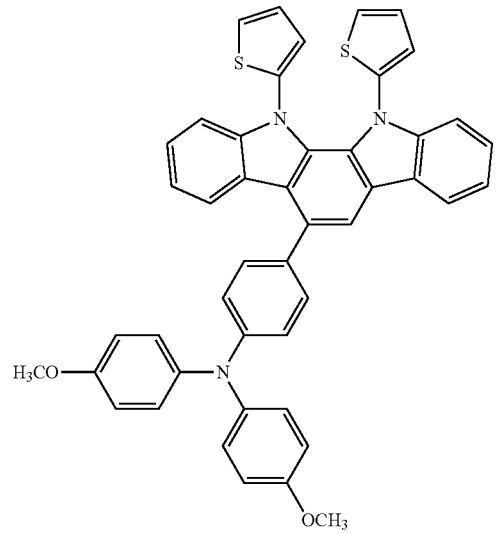
[Chemical 74]
(Compound 69)
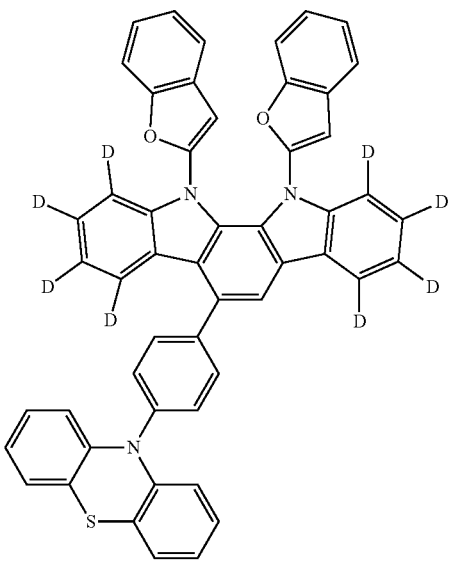

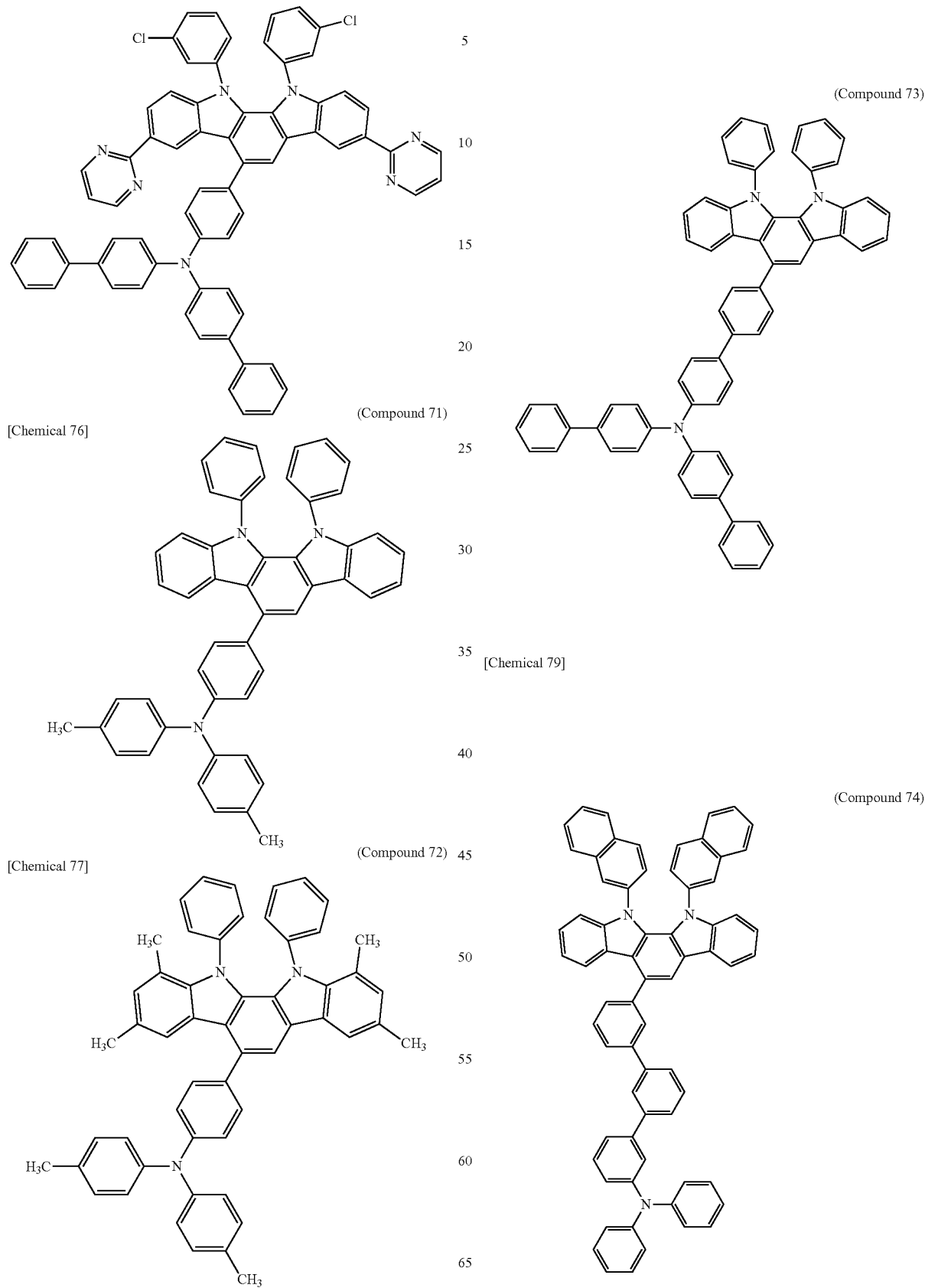

[Chemical 80] (Compound 75)

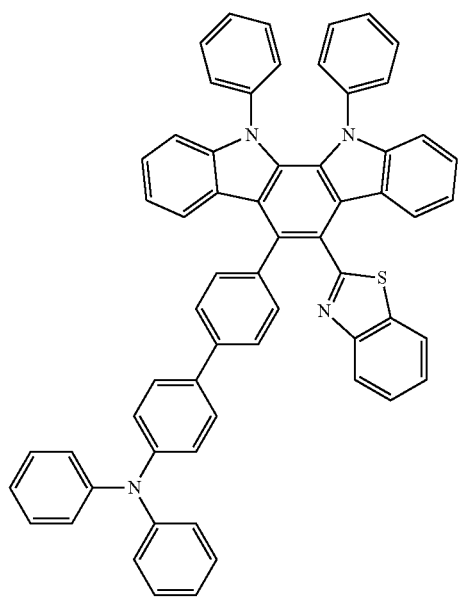

[Chemical 81] (Compound 76)

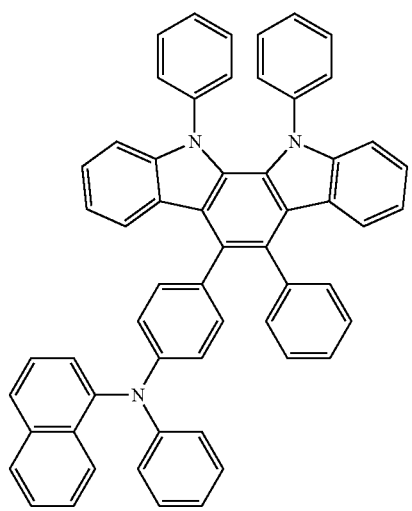

[Chemical 82] (Compound 77)

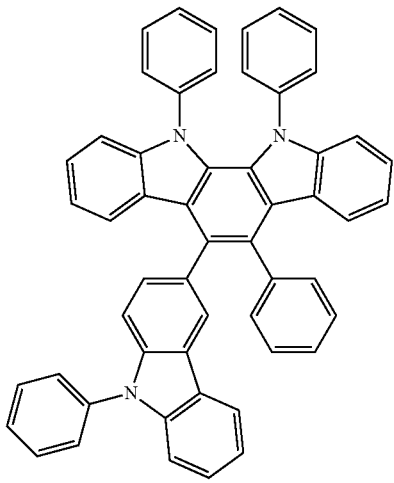

(Use)

The compounds having the indolocarbazole ring structure of the invention shown above are novel compounds having, for example, high glass transition points (Tg) of not lower than 100° C. and, specifically, not lower than 150° C. as demonstrated in Examples appearing later. Such high glass transition points (Tg) make it possible to form thin films having excellent heat resistance maintaining stability in their amorphousness and in their form of thin films.

Measurement of the films of a thickness of 100 nm formed by depositing the compounds of the present invention shows work functions that are higher than those of the known hole-transporting materials such as NPD and TPD.

From the above point of view, the compound having the indolocarbazole ring structure of the present invention can be used as a material for constituting the hole injection layer and/or the hole-transporting layer of the organic EL devices. Namely, by forming the hole injection layer and the hole-transporting layer by using the compound of the present invention, it is allowed to improve the hole injection property, to increase the mobility thereof, to enhance the electron blocking power, to increase stability for electrons, to confine the formed excitons within the luminous layer of the device, to increase the probability of recombination of holes with electrons, to obtain a high luminous efficiency, to lower the driving voltage and to improve durability of the organic EL device.

Further, the compound of the present invention can also be used as a material for constituting the electron blocking layer of the organic EL device. Upon using the compound of the present invention having excellent electron blocking power, superior positive electron-transporting property to those of the prior materials and high stability in the form of a thin film, it is allowed to lower the driving voltage, to improve resistance against the electric current and to improve maximum luminous brightness of the organic EL device yet maintaining a high luminous efficiency.

The compound of the present invention can also be used as a material for constituting the luminescent layer of the organic EL devices. By using the material of the invention that excels in the hole-transporting property as compared to the conventional materials and has a wide band gap as a host material of the luminous layer and by forming the luminous layer in a manner to carry a fluorescent luminous body or a phosphorescent luminous body that is called dopant, it is made possible to realize an organic EL device which requires a decreased driving voltage and features an improved luminous efficiency.

(Organic EL Device)

The organic EL device formed by using the above-mentioned compound of the invention representatively has a structure in which an anode, a hole-transporting layer, an electron blocking layer, a luminous layer, an electron-transporting layer and a cathode are formed in this order on a predetermined substrate (e.g., a glass substrate or a transparent resin substrate) though the invention is in no way limited to this structure only.

For instance, a hole injection layer can be provided between the anode and the hole-transporting layer, and an electron injection layer can be formed between the electron-transporting layer and the cathode.

Further, some of the layers can be omitted from the above multilayered structure. For instance, the structure may be the one in which an anode, a hole-transporting layer, a luminous layer, an electron-transporting layer and a cathode are formed successively on the substrate.

The above-mentioned compound of the invention is used for forming the hole-transporting layer, hole injection layer, electron blocking layer and luminous layer in the above multilayered structure.

The anode of the organic EL device may be formed by using an electrode material that has been known per se. i.e., by using an electrode material having a large work function, such as ITO or gold.

In addition to using the compound having the indolocarbazole ring structure represented by the general formula (1) of the invention described above, the hole injection layer can also be formed by using a porphyrin compound as represented by copper phthalocyanine, star burst-type triphenylamine derivatives, various triphenylamine tetramers, acceptor-type heterocyclic compound such as hexacyanoazatriphenylene or a coating-type high molecular material. By using these materials, a thin film can be formed by a known method such as vacuum evaporation method, spin-coating method or ink-jet method. A variety of layers described below can also be formed by vacuum evaporation, spin coating or ink jet.

In addition to using the compound of the present invention, the hole-transporting layer can also be formed by using known hole-transporting materials.

Described below are representative examples of the hole materials.

Benzidine derivatives such as:
  N,N'-diphenyl-N,N'-di(m-tolyl)benzidine (hereinafter abbreviated as TPD);
  N,N'-diphenyl-N,N'-di(α-naphthyl)benzidine (hereinafter abbreviated as NPD);
  and
  N,N,N',N'-tetrabiphenylylbenzidine;
Amine derivatives such as:
  1,1-bis[4-(di-4-tolylamino)phenyl]cyclohexane (hereinafter abbreviated as TAPC);
  and
  various triphenylamine trimers and tetramers.

The above known hole-transporting material compounds inclusive of the compounds of the present invention may be used in a single kind or may be used being mixed together in two or more kinds to form a film. Further, a plurality of layers may be formed by using any one kind of the above compounds or a plurality of kinds of the above compounds, and a multilayered film of a laminate of such layers may be used as the hole-transporting layer.

The hole injection layer or the hole-transporting layer can be formed by using a high molecular material of the coating type, such as poly(3,4-ethylenedioxythiophene (hereinafter abbreviated as PEDOT) or poly(styrene sulfonate) (hereinafter abbreviated as PSS).

As the hole injection layer or the hole-transporting layer, further, there can be used a material that is usually used but is, further, P-doped with a trisbromophenylaminehexachloroantimony or the like or a high molecular compound having the TPD structure as part of its structure.

In addition to using the above compound of the present invention, the electron blocking layer can also be formed by using known compounds having the electron blocking power, such as carbazole derivatives or a compound having a triphenylsylyl group and a triarylamine structure. Concrete examples of the compound having carbazole derivatives and the triarylamine structure are as follows:

<Carbazole Derivatives>
  4,4',4''-tri(N-carbazolyl)triphenylamine (hereinafter abbreviated as TCTA);
  9,9-bis[4-(carbazole-9-il)phenyl]fluorene;
  1,3-bis(carbazole-9-il)benzene (hereinafter abbreviated as mCP);
  and
  2,2-bis(4-carbazole-9-ilphenyl)adamantane (hereinafter abbreviated as Ad-Cz)
<Compounds Having the Triarylamine Structure>
  9-[4-(carbazole-9-il)phenyl]-9-[4-(triphenylsylyl)phenyl]-9H-fluorene The above electron blocking layer, too, is formed by using the compound of the present invention or the known hole-transporting material compound in one kind or in two or more kinds. It is here allowable to form a plurality of layers by using one or a plurality of kinds of these compounds and to use a multilayered film of a laminate of such layers as the electron blocking layer.

The luminous layer of the organic EL device is formed by using a luminous material such as $Alq_3$ or a metal complex of a quinolinol derivative, various metal complexes of zinc, beryllium or aluminum, anthracene derivative, bisstyrylbenzene derivative, pyrene derivative, oxazole derivative or polyparaphenylenevinylene derivative.

It is also allowable to constitute the luminous layer by using a host material and a dopant material. As the host material in this case, there can be used the above-mentioned compound having the indolocarbazole ring structure of the present invention. In addition to using the compounds of the present invention, there can be further used, as the host material, the above luminous materials as well as thiazole derivatives, benzimidazole derivatives and polydialkylfluorene derivatives.

As the dopant material, there can be used quinacridone, cumalin, rubrene, perylene and derivatives thereof, benzopyran derivatives, rhodamine derivatives and aminostyryl derivatives.

The above luminous layer, too, may be formed in a single-layer constitution using one or two or more kinds of luminous materials or may be formed in a multilayered structure by laminating a plurality of layers.

The luminous layer can be, further, formed by using a phosphorescent luminous material as the luminous material. As the phosphorescent luminous material, there can be used a phosphorescent luminous body of a metal complex of iridium or platinum. For instance, there can be used a green phosphorescent luminous body such as $Ir(ppy)_3$, a blue phosphorescent luminous body such as FIrpic or $FIr_6$, or a red fluorescent luminous body such as $Btp_2Ir(acac)$. These phosphorescent luminous materials are used being added to the hole injection/transport host material and to the electron-transporting host material.

As the hole-transporting host material, there can be used the compound of the present invention in addition to the carbazole derivatives such as 4,4'-di(N-carbazolyl)biphenyl (hereinafter abbreviated as CBP), TCTA and mCP.

As the electron-transporting host material, there can be used a p-bis(triphenylsylyl)benzene (hereinafter abbreviated as UGH2) and a 2,2',2''-(1,3,5-phenylene)-tris(1-phenyl-1H-benzimidazole) (hereinafter abbreviated as TPBI).

In order to avoid the concentration quenching, it is desired that the host material is doped with the phosphorescent luminous material by the vacuum co-evaporation in an amount in a range of 1 to 30% by weight per the whole luminous layer.

As the hole blocking layer of the organic EL device, there can be used a compound having the hole blocking action that has been known per se.

As the compound having the hole blocking action, there can be exemplified metal complexes of phenanthroline derivatives such as basocuproin (hereinafter abbreviated as BCP) and aluminum(III)bis(2-methyl-8-quinolinato)-4-phenylphenolate (hereinafter abbreviated as BAlq), as well as triazole derivatives, triazine derivatives and oxadiazole derivatives.

There materials may be also used as the material of the electron-transporting layer.

The hole blocking layer, too, may be formed as a single layer or a laminate of a multiplicity of layers, each layer being formed by using one kind, two kind or more kinds of the above-mentioned compounds having the hole blocking action.

The electron-transporting layer of the organic EL device is formed by using an electron-transporting compound such as $Alq_3$, BAlq, a metal complex of quinolinol derivative, or various metal complexes of zinc, beryllium or aluminum, or triazole derivatives, triazine derivatives, oxadiazole derivatives, thiadiazole derivatives, carbodiimide derivatives, quinoxaline derivatives, phenanthroline derivatives or silole derivatives.

The electron-transporting layer, too, may be formed as a single layer or a laminate of a multiplicity of layers, each layer being formed by using one kind, two kind or more kinds of the above-mentioned electron-transporting compounds.

Like the known one, further, the electron injection layer of the organic EL device can be formed by using an alkali metal salt such as lithium fluoride or cesium fluoride, an alkaline earth metal salt such as magnesium fluoride, or a metal oxide such as aluminum oxide, which, however, may be omitted in a preferred selection of the electron-transporting layer and the cathode.

As the cathode of the organic EL device, there is used an electrode material having a low work function, such as aluminum, or an electrode material having a lower work function, such as magnesium silver alloy, magnesium indium alloy or aluminum magnesium alloy.

EXAMPLES

Example 1

Synthesis of a 5-(9-phenyl-9H-carbazole-3-il)-11, 12-diphenylindolo[2,3-a]carbazole (compound 4)

Into a reactor purged with nitrogen, there were added:

| | |
|---|---|
| 11,12-Dihydroindolo[2,3-a] carbazole, | 15.0 g |
| Iodobenzene, | 19.6 ml |
| Copper powder, | 0.37 g |
| 3,5-Di(tert-butyl)salicylic acid, | 1.47 g |
| Potassium carbonate, | 12.13 g |
| Dodecylbenzene, | 25 ml | which were then heated at 200° C. and stirred for 7 hours. After cooled down to 100° C., 400 ml of toluene was added thereto to dissolve them, and the insoluble matter was removed by filtration.

After condensed under reduced pressure, the condensate was crystallized with 500 ml of methanol to obtain 22.6 g of a white powder of 11,12-diphenylindolo[2,3-a]carbazole (yield, 94.5%).

Next, into the reactor, there were added:

| | |
|---|---|
| White powder of the carbazole obtained above, | 22.6 g |
| DMF: | 300 ml |
| Imide N-bromosuccinate, | 9.36 g | which were stirred at room temperature for 8 hours and were, thereafter, left to stand overnight.

Next, the reaction solution was added to 1000 ml of water, and the crude product was collected by filtration, washed with water and, then, with methanol to obtain 26.3 g of a powder of 5-bromo-11,12-diphenylindolo[2,3-a]carbazole (yield, 100%).

Next, into the reactor that has been purged with nitrogen, there were added:

| | |
|---|---|
| Powder of the bromo-formed carbazole obtained above, | 3.80 g |
| 9-Phenyl-3-(4,4,5,5-tetramethyl-1,3,2-dioxaborolane-2-il)-9H-carbazole, | 2.88 g |
| A mixed solvent of toluene/ethanol (4/1, v/v), | 35 ml |
| 2M potassium carbonate aqueous solution, | 12 ml | and the ventilation was conducted with a nitrogen gas for 30 minutes while being irradiated with ultrasonic waves.

Further, 0.24 g of a tetrakis(triphenylphosphine) palladium (0) was added thereto and was heated, refluxed and stirred for 15 hours. After cooled down to room temperature, 50 ml of toluene and 20 ml of water were added thereto, followed by the separating operation to correct the organic layer. Further, the aqueous layer was extracted with 20 ml of toluene to collect the organic layer. After the organic layers were added up together, water was removed with anhydrous magnesium sulfate, and a crude product was obtained by the condensation under reduced pressure.

The obtained crude product was purified by the column chromatography (carrier: silica gel, eluent: toluene/cyclohexane) to obtain 1.69 g of a light yellow powder of 5-(9-phenyl-9H-carbazole-3-il)-11,12-diphenylindolo[2,3-a]carbazole that corresponded to the above-mentioned compound 4 (yield, 33.3%).

The obtained light yellow powder was identified for its structure relying on the NMR. FIG. 1 shows the results of the $^1$H-NMR measurement.

The following 31 signals of hydrogen were detected by the $^1$H-NMR (THF-$d_8$). The results were as follows:

$\delta(ppm) = 8.54(1H)$ 8.18-8.22(2H)

8.09(1H)

7.76-7.80(3H)

7.70-7.72(2H)

7.63-7.64(1H)

7.52-7.54(1H)

7.49-7.50(1H)

7.41-7.44(2H)

-continued 7.22-7.30(5H)

7.13-7.16(7H)

6.83-6.88(5H)

Example 2

Synthesis of a 5-[{biphenyl-4-il)phenylamino}phenyl-4-il]-11,12-diphenylindolo[2,3-a]carbazole (compound 12)

Into the reactor purged with nitrogen, there were added:

| | |
|---|---|
| 5-Bromo-11,12-diphenylindolo[2,3-a] carbazole synthesized in Example 1, | 3.40 g |
| (Biphenyl-4-il)-{4-(4,4,5,5-tetramethyl-1,3,2-dioxaborane-2-il) phenyl}-phenylamine, | 3.12 g |
| Mixed solvent of toluene/ethanol (4/1, v/v), | 30 ml |

2M potassium carbonate aqueous solution, 10.5 ml, and the ventilation was conducted with the nitrogen gas for 30 minutes while being irradiated with ultrasonic waves. Next, 0.24 g of the tetrakis(triphenylphosphine) palladium (0) was added thereto and was heated, refluxed and stirred for 13 hours. After cooled down to room temperature, 50 ml of toluene and 50 ml of water were added thereto, followed by the separating operation to collect the organic layer. Further, the aqueous layer was extracted with 30 ml of toluene to collect the organic layer. After the organic layers were added up together, water was removed with anhydrous magnesium sulfate, and a crude product was obtained by the condensation under reduced pressure.

In the same manner as in Example 1, the crude product was purified by the column chromatography and was, further, washed with hexane to obtain 3.68 g of a light yellow powder of 5-[{(biphenyl-4-il)-phenylamino}phenyl-4-il]-11,12-diphenylindolo[2,3-a]carbazole that corresponded to the above-mentioned compound 12 (yield, 72.4%).

Figure 2:
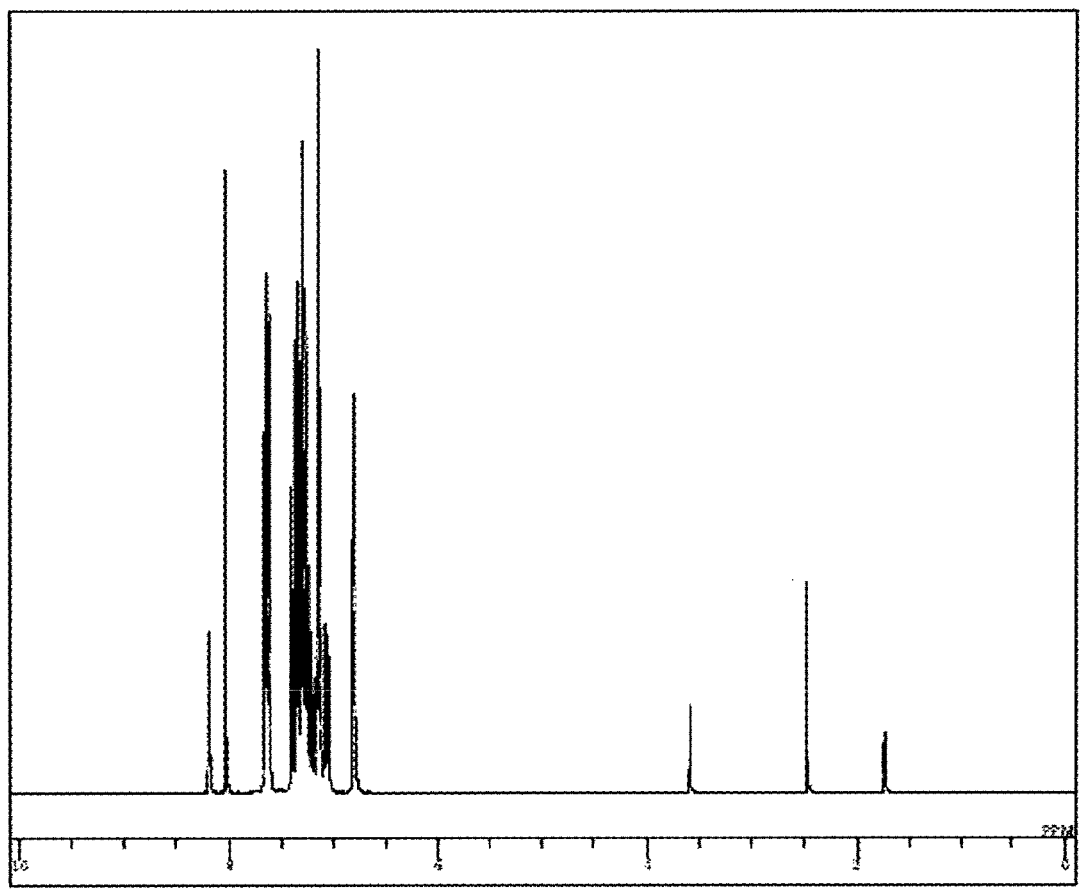
FIG. 2 is a $^1$H-NMR chart of a compound (compound 12) of Example 2 of the invention.

The obtained light yellow powder was identified for its structure relying on the NMR. FIG. 2 shows the results of the $^1$H-NMR measurement.

The following 37 signals of hydrogen were detected by the $^1$H-NMR (THF-d$_8$). The results were as follows:

$\delta$(ppm) = 8.17-8.18(1H)

8.02(1H)

8.09(1H)

7.61-7.66(7H)

7.03-7.41(24H)

6.79-6.81(4H)

Example 3

Synthesis of a 5-[{bis(phenyl-4-il)amino}phenyl-4-il]-11,12-diphenylindolo[2,3-a]carbazole (compound 13)

Into the reactor purged with nitrogen, there were added:

| | |
|---|---|
| 5-Bromo-11,12-diphenylindolo[2,3-a] carbazole synthesized in Example 1, | 3.40 g |
| Bis(biphenyl-4-il)-{4-(4,4,5,5-tetramethyl-1,3,2-dioxaborane-2-il)phenyl} amine, | 3.22 g |
| Mixed solvent of toluene/ethanol (4/1, v/v), | 30 ml |
| 2M potassium carbonate aqueous solution, | 9.2 ml, | and the ventilation was conducted with the nitrogen gas for 30 minutes while being irradiated with ultrasonic waves. Further, 0.43 g of the tetrakis(triphenylphosphine) palladium (0) was added thereto and was heated, refluxed and stirred for 8 hours. After cooled down to room temperature, 50 ml of toluene and 50 ml of water were added thereto, followed by the separating operation to collect the organic layer. The organic layer was dehydrated with the anhydrous magnesium sulfate, and a crude product was obtained by the condensation under reduced pressure.

The crude product was successively subjected to the adsorptive purification with an NH silica gel, crystallization by using a mixed solvent of ethyl acetate and n-hexane, washing with ethyl acetate, recrystallization with toluene, crystallization with a mixed solvent of toluene and n-hexane, and washing with methanol to obtain 2.92 g of a white powder of 5-[{bis(biphenyl-4-il)amino}phenyl-4-il]-11,12-diphenylindolo[2,3-a]carbazole that corresponded to the compound 13 (yield, 59.1%).

Figure 3:
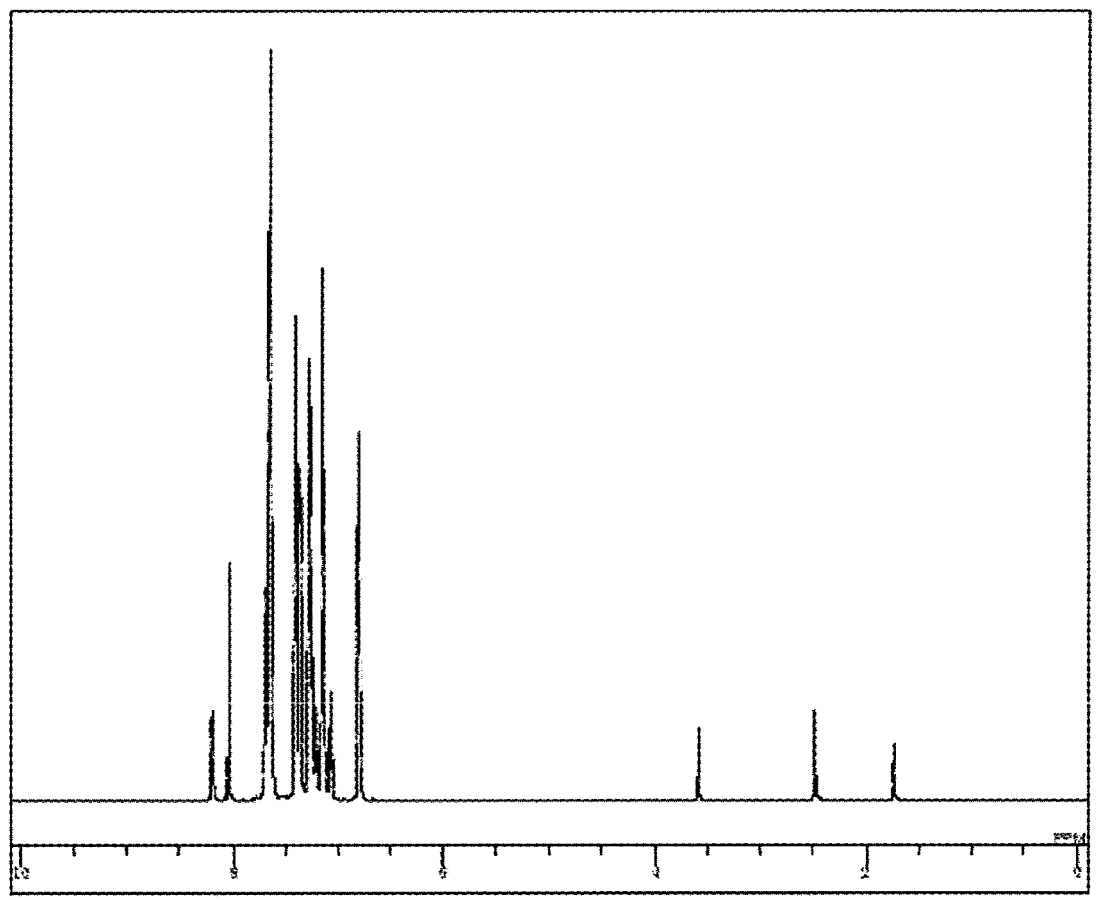
FIG. 3 is a $^1$H-NMR chart of a compound (compound 13) of Example 3 of the invention.

The obtained white powder was identified for its structure relying on the NMR. FIG. 3 shows the results of the $^1$H-NMR measurement.

The following 41 signals of hydrogen were detected by the $^1$H-NMR (THF-d$_8$). The results were as follows:

$\delta$(ppm) = 8.18-8.19(1H)

8.04(1H)

7.64-7.69(11H)

7.34-7.40(10H)

7.05-7.27(14H)

6.80(4H)

Example 4

Synthesis of a 5-[{(biphenyl-4-il)-phenylamino}phenyl-4-il]-6,11,12-triphenylindolo[2,3-a]carbazole (compound 17)

Into the reactor purged with nitrogen, there were added:

| | |
|---|---|
| 5-Bromo-11,12-diphenylindolo[2,3-a] carbazole synthesized in Example 1, | 100 g |
| Phenylboronic acid, | 25.0 g |
| Mixed solvent of toluene/ethanol (4/1, v/v), | 1000 ml |
| 2M potassium carbonate aqueous solution, | 205 ml, | and the ventilation was conducted with the nitrogen gas for 30 minutes while being irradiated with ultrasonic waves. Further, 2.37 g of the tetrakis(triphenylphosphine) palladium (0) was added thereto and was heated, refluxed and stirred for 8 hours. After cooled down to room temperature, 500 ml of toluene and 100 ml of water were added thereto, followed by the separating operation to collect the organic layer. Further, the aqueous layer was extracted with 200 ml of toluene to collect the organic layer. After the organic layers were added up together, water was removed with the anhydrous magnesium sulfate, and a crude product was obtained by the condensation under reduced pressure.

The crude product was successively subjected to the adsorptive purification with silica gel, crystallization by using a mixed solvent of ethyl acetate and methanol, crystallization by using a mixed solvent of toluene and n-hexane, washing with ethyl acetate, crystallization by using a mixed solvent of 1,2-dichlorobenzene and methanol, and washing with methanol to obtain 57.8 g of a powder of 5,11,12-triphenylindolo[2,3-a]carbazole (yield, 58.2%).

Next, into the reactor, there were added:

| | |
|---|---|
| Triphenylated carbazole powder obtained above, | 68.0 g |
| DMF: | 680 ml |
| Imide N-bromosuccinate, | 25.0 g | which were stirred at room temperature for 6 hours and were, thereafter, left to stand overnight. 1000 Milliliters of water was added to the reaction solution, and the crude product was collected by filtration and was successively subjected to the washing with methanol and crystallization by using the mixed solvent of toluene and n-hexane to obtain 58.4 g of a powder of 5-bromo-6,11,12-triphenylindolo[2,3-a]carbazole (yield, 73.9%).

Next, into the reactor that has been purged with nitrogen, there were added:

| | |
|---|---|
| Bromonated carbazole powder obtained above, | 15.0 g |
| (Biphenyl-4-il)-{4-(4,4,5,5-tetramethyl-1,3,2-dioxa borane-2-il)phenyl}-phenylamine, | 13.1 g |
| A mixed solvent of toluene/ethanol (4/1, v/v), | 150 ml |
| 2M potassium carbonate aqueous solution, | 26.6 ml | and the ventilation was conducted with the nitrogen gas for 30 minutes while being irradiated with ultrasonic waves. Further, 0.62 g of the tetrakis(triphenylphosphine) palladium (0) was added thereto and was heated, refluxed and stirred for 6 hours. After cooled down to room temperature, 100 ml of water and 200 ml of methanol were added thereto, and the crude product was collected by filtration.

The crude product was dissolved in a 1,2-dichlorobenzene, and was successively subjected to the dehydration with magnesium sulfate, adsorptive purification with silica gel, washing with ethyl acetate, crystallization by using a mixed solvent of 1,2-dichlorobenzene and ethyl acetate, washing with toluene, and washing with methanol to obtain 12.8 g of a white powder of 5-[{(biphenyl-4-il)-phenylamino}phenyl-4-il]-6,11,12-triphenylindolo[2,3-a]carbazole corresponding to the compound 17 (yield, 59.6%).

Figure 4:
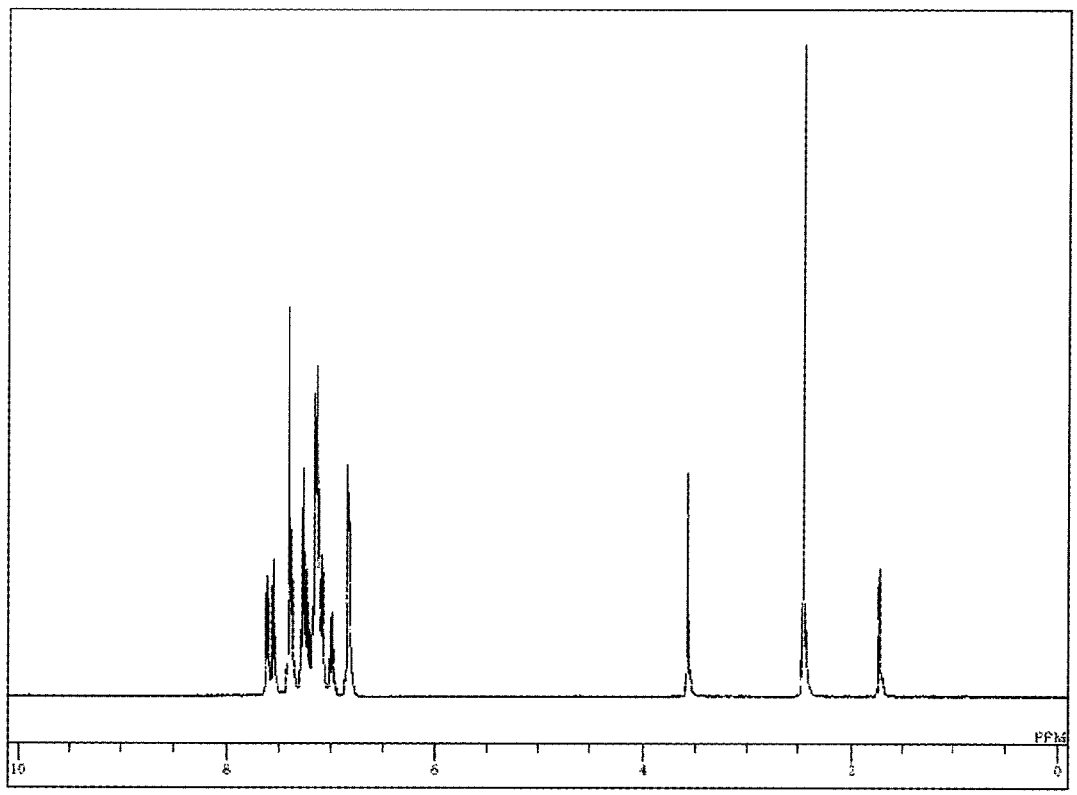
FIG. 4 is a $^1$H-NMR chart of a compound (compound 17) of Example 4 of the invention.

The obtained white powder was identified for its structure relying on the NMR. FIG. 4 shows the results of the $^1$H-NMR measurement.

The following 41 signals of hydrogen were detected by the $^1$H-NMR (THF-d$_8$). The results were as follows:

$\delta$(ppm) = 7.59(4H)

7.40(7H)

7.09-7.29(22H)

7.01(2H)

6.85(6H)

Example 5

Synthesis of a 5-[{(naphthalene-1-il)-phenylamino}phenyl-4-il]-6,11,12-triphenylindolo[2,3-a]carbazole (compound 76)

Into the reactor purged with nitrogen, there were added:

| | |
|---|---|
| 5-Bromo-6,11,12-triphenylindolo[2,3-a]carbazole synthesized in Example 4, | 15.0 g |
| (Naphthalene-1-il)-{4-(4,4,5,5-tetramethyl-1,3,2-dioxaborane-2-il)phenyl}-phenylamine, | 12.3 g |
| Mixed solvent of toluene/ethanol (4/1, v/v), | 150 ml |
| 2M potassium carbonate aqueous solution, | 26.6 ml, | and the ventilation was conducted with the nitrogen gas for 30 minutes while being irradiated with ultrasonic waves. Further, 0.62 g of the tetrakis(triphenylphosphine) palladium (0) was added thereto and was heated, refluxed and stirred for 13 hours. After cooled down to room temperature, 100 ml of water and 200 ml of ethyl acetate were added thereto, and the crude product was collected by filtration.

The crude product was dissolved in the 1,2-dichlorobenzene and was successively subjected to the dehydration with magnesium sulfate, adsorptive purification with silica gel, crystallization by using a mixed solvent of 1,2-dichlorobenzene and methanol, and washing with methanol to obtain 13.1 g of a white powder of 5-[{(naphthalene-1-il)-phenylamino}phenyl-4-il]-6,11,12-triphenylindolo[2,3-a]carbazole corresponding to the compound 76 (yield, 63.2%).

Figure 5:
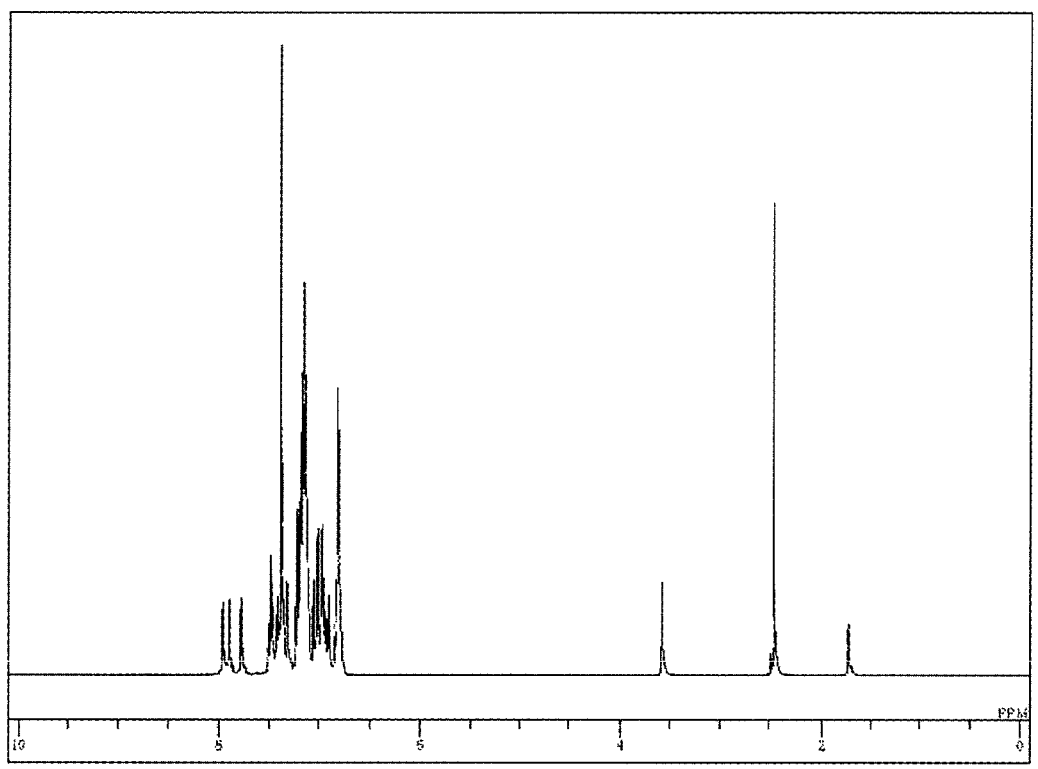
FIG. 5 is a $^1$H-NMR chart of a compound (compound 76) of Example 5 of the invention.

The obtained white powder was identified for its structure relying on the NMR. FIG. 5 shows the results of the $^1$H-NMR measurement.

The following 39 signals of hydrogen were detected by the $^1$H-NMR (THF-d$_8$). The results were as follows:

$\delta$(ppm) = 7.93(2H)

7.78(1H)

7.31-7.50(9H)

7.19(14H)

6.99(7H)

6.83(6H)

Example 6

Synthesis of a 5-(9-phenyl-9H-carbazole-3-il)-6,11,12-triphenylindolo[2,3-a]carbazole (compound 77)

Into the reactor purged with nitrogen, there were added:

| | |
|---|---|
| 5-Bromo-6,11,12-triphenylindolo[2,3-a]carbazole synthesized in Example 4, | 8.00 g |
| 9-Phenyl-3-(4,4,5,5-tetramethyl-1,3,2-dioxaborane-2-il)-9H-carbazole, | 5.24 g |
| Mixed solvent of toluene/ethanol (4/1, v/v), | 160 ml |
| 2M potassium carbonate aqueous solution, | 14.2 ml, | and the ventilation was conducted with the nitrogen gas for 30 minutes while being irradiated with ultrasonic waves. Further, 0.32 g of the tetrakis(triphenylphosphine) palladium (0) was added thereto and was heated, refluxed and stirred for 6 hours. After cooled down to room temperature, 200 ml of toluene and 50 ml of water were added thereto, followed by the separation operation to collect the organic layer. Further, the aqueous layer was extracted with 150 ml of toluene to collect the organic layer. After the organic layers were added up together, water was removed with the anhydrous magnesium sulfate, and a crude product was obtained by the condensation under reduced pressure.

The crude product was successively subjected to the adsorptive purification with silica gel, crystallization by using a mixed solvent of 1,2-dichlorobenzene and methanol, and washing with methanol to obtain 6.76 g of a white powder of 5-(9-phenyl-9H-carbazole-3-il)-6,11,12-triphenylindolo[2,3-a]carbazole corresponding to the compound 77 (yield, 65.6%).

Figure 6:
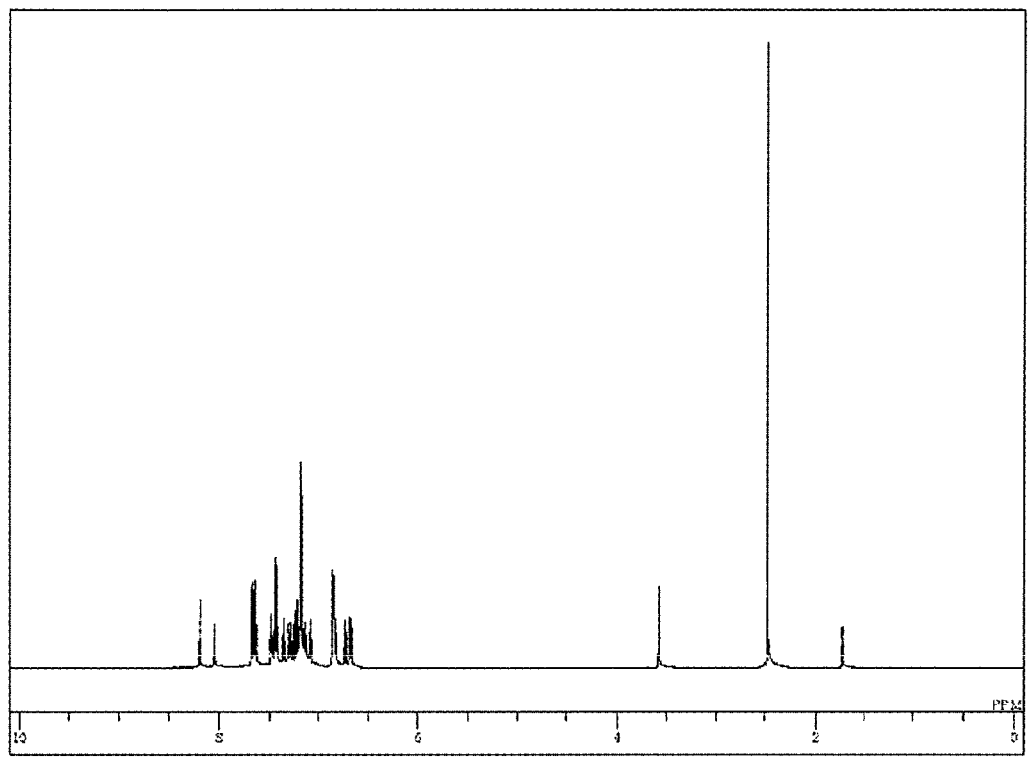
FIG. 6 is a $^1$H-NMR chart of a compound (compound 77) of Example 6 of the invention.

The obtained white powder was identified for its structure relying on the NMR. FIG. 6 shows the results of the $^1$H-NMR measurement.

The following 35 signals of hydrogen were detected by the $^1$H-NMR (THF-$d_8$). The results were as follows:

$\delta$(ppm) = 8.20(1H)

8.05(1H)

7.64-7.69(4H)

7.45(6H)

7.35(1H)

7.29(2H)

7.12-7.25(11H)

Example 7

The compounds of the invention obtained in Examples 1 to 6 above were measured for their glass transition points (Tg).

The glass transition points were measured by using a highly sensitive differential scanning calorimeter (DSC 3100S manufactured by Bruker AXS Co.). The results were as follows:

| | Glass transition point |
|---|---|
| Compound of Example 1 (compound 4) | 182° C. |
| Compound of Example 2 (compound 12) | 153° C. |
| Compound of Example 3 (compound 13) | 171° C. |
| Compound of Example 4 (compound 17) | 160° C. |
| Compound of Example 5 (compound 76) | 161° C. |
| Compound of Example 6 (compound 77) | 203° C. |

As will be understood from the above results, the compounds of the present invention have glass transition points of not lower than 100° C. and, specifically, not lower than 150° C. showing that the thin films formed by using the compounds of the present invention remain stable.

Example 8

By using the compounds of the invention obtained in Examples 1 to 3 above, films were formed in a thickness of 100 nm on the ITO substrates by vacuum evaporation and were measured for their work functions by using a photoelectron spectrometer (Model AC-3, manufactured by Riken Keiki Co.) in the atmosphere.

| | Work function |
|---|---|
| Compound of Example 1 | 5.64 eV |
| Compound of Example 2 | 5.52 eV |
| Compound of Example 3 | 5.51 eV |

As described above, the compounds of the invention have favorable energy levels as compared to the work function of 5.4 eV possessed by general hole-transporting materials such as NPD and TPD, and, therefore, have favorable hole-transporting capabilities.

Example 9

Figure 7:
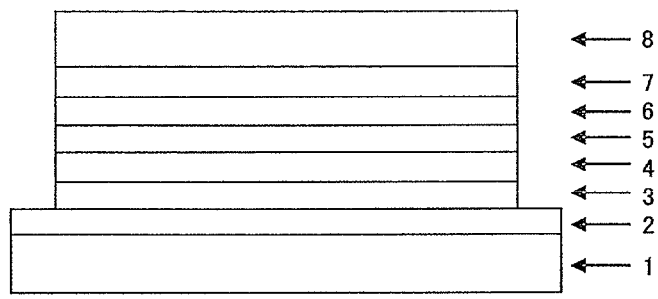
FIG. 7 is a view illustrating the constitution of EL devices of Examples 9 and 10, and of Comparative Example 1.

An organic EL device of a structure shown in FIG. 7 was fabricated by using the compound of Example 3, and was evaluated.

That is, the organic EL device was fabricated by, first, forming a transparent anode 2 (ITO electrode) on a glass substrate 1 and, thereafter, successively forming, on the transparent electrode 2, a hole injection layer 3, a hole-transporting layer 4, a luminous layer 5, an electron-transporting layer 6, an electron injection layer 7 and a cathode (aluminum electrode) 8 in this order. Concretely, the organic EL device was fabricated in a manner as described below.

First, the glass substrate 1 on which the ITO film (transparent electrode 2) has been formed in a thickness of 150 nm was washed with an organic solvent and was, thereafter, washed for its surface by an oxygen plasma treatment.

Thereafter, the glass substrate 1 with the transparent electrode was placed in a vacuum evaporation apparatus, and the pressure therein was reduced down to 0.001 Pa or lower.

Next, as the hole injection layer 3, a film of the compound 78 of the following structural formula was formed in a thickness of 20 nm so as to cover the transparent anode 2.

[Chemical 83]

(Compound 78)

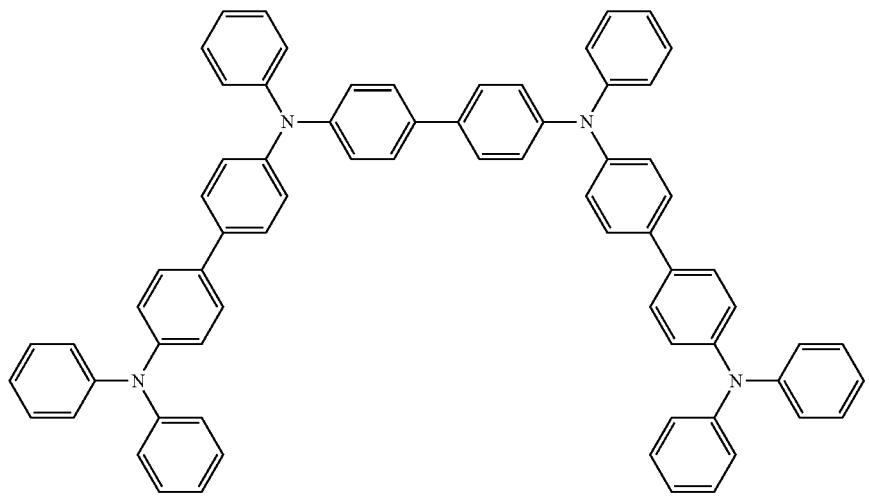

As the hole-transporting layer 4, a film of the compound (compound 13) synthesized in Example 3 was formed in a thickness of 40 nm on the hole injection layer 3.

As the luminous layer 5, a film was formed in a thickness of 30 nm on the hole-transporting layer 4 by conducting the two-way vacuum evaporation, i.e., by depositing the compound 79 of the following structural formula and the compound 80 of the following structural formula at a deposition rate of compound 79:compound 80=5:95.

As the electron-transporting layer 6, a film of Alq$_3$ was formed in a thickness of 30 nm on the luminous layer 5. As the electron injection layer 7, a film of lithium fluoride was formed in a thickness of 0.5 nm on the electron-transporting layer 6. Finally, aluminum was deposited to be 150 nm in thickness to form the cathode 8.

A DC voltage was applied to the thus fabricated organic EL device at normal temperature in the atmosphere to measure its luminous properties which were as summarized in Table 1.

[Chemical 84]

(Compound 79)

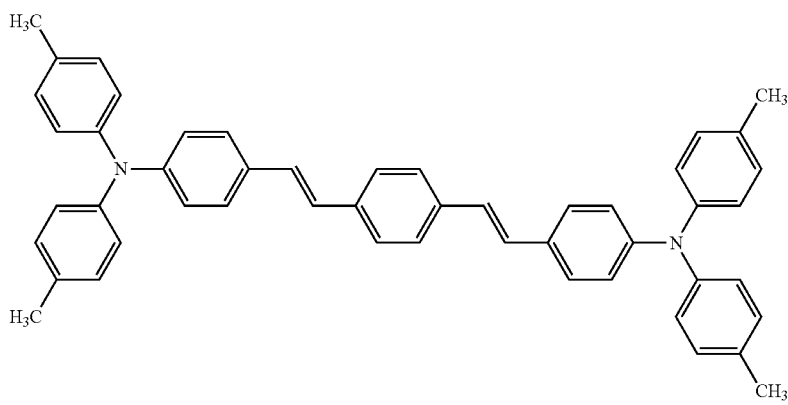

[Chemical 85]

(Compound 80)

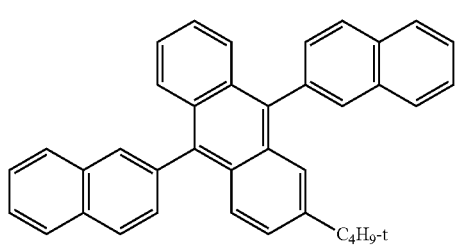

Example 10

An organic EL device was fabricated under the same conditions as in Example 9 but using, as the material of the hole-transporting layer 4, the compound (compound 12) of Example 2 instead of the compound (compound 13) of Example 3 and forming the hole-transporting layer 4 in a thickness of 40 nm.

A DC voltage was applied to the thus fabricated organic EL device at normal temperature in the atmosphere to measure its luminous properties which were as summarized in Table 1.

Comparative Example 1

For comparison, an organic EL device was fabricated under the same conditions as in Example 9 but using, as the material of the hole-transporting layer 4, the compound 81 of the following structural formula instead of the compound (compound 13) of Example 3.

A DC voltage was applied to the thus fabricated organic EL device at normal temperature in the atmosphere to measure its luminous properties which were as summarized in Table 1.

[Chemical 86]

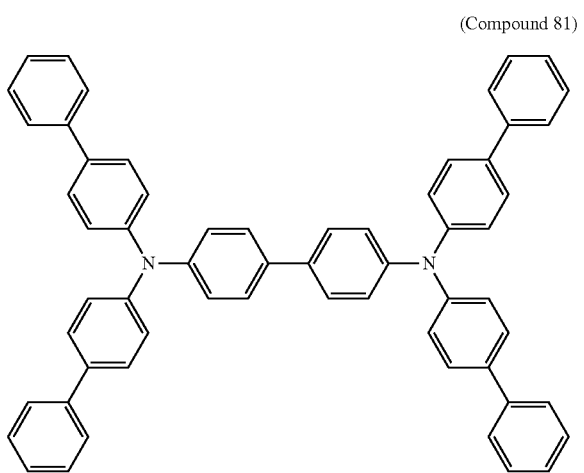

(Compound 81)

TABLE 1

| Compound | Voltage [V] (@10 mA/ cm$^2$) | Brightness [cd/m$^2$] (@10 mA/ cm$^2$) | Luminous efficiency [cd/A] (@10 mA/ cm$^2$) | Power efficiency [lm/W] (@10 mA/ cm$^2$) |
|---|---|---|---|---|
| Ex. 9 compound 13 | 5.07 | 1031 | 10.31 | 6.39 |
| Ex. 10 compound 12 | 4.88 | 1031 | 10.34 | 6.66 |
| Comp. Ex. 1 compound 81 | 5.17 | 902 | 9.03 | 5.49 |

It is learned from Table 1 that when an electric current was flown at a density of 10 mA/cm$^2$, the driving voltage was 5.17 V in Comparative Example 1 that used the compound 81 of the above structural formula, but was 5.07 V in Example 9 that used the compound (compound 13) of Example 3 and was 4.88 V in Example 10 that used the compound (compound 12) of Example 2. It was, therefore, learned that the driving voltages were low when the compounds of the present invention were used.

The power efficiency was 5.49 lm/W in Comparative Example 1, which, however, greatly increased to 6.39 lm/W in Example 9 that used the compound (compound 13) of Example 3 and to 6.66 lm/W in Example 10 that used the compound (compound 12) of Example 2.

As is obvious from the above results, it was learned that the organic EL devices using the compounds having the indolocarbazole ring structure of the present invention achieved improved power efficiency and decreased practical driving voltage as compared to the organic EL device that used the known compound 81.

INDUSTRIAL APPLICABILITY

The compounds having the indolocarbazole ring structure of the present invention feature high hole-transporting capabilities, high electron blocking power, excellent amorphousness, stability in the form of thin film, and are excellent compounds for use in the organic EL devices. By producing the organic EL devices by using the above compounds, it is allowed to attain a high luminous efficiency, a high power efficiency, a low practical driving voltage and improved durability, expanding the use in the field of domestic electric appliances and lighting fixtures.

DESCRIPTION OF REFERENCE NUMERALS

1: glass substrate
2: transparent anode
3: hole injection layer
4: hole-transporting layer
5: luminous layer
6: electron-transporting layer
7: electron injection layer
8: cathode

The invention claimed is:

1. A compound having an indolocarbazole ring structure of the following formula (1),

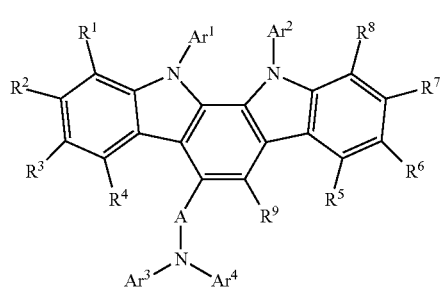

(1)

wherein,
A is a phenylene group,
A and Ar$^4$ are bonded together to form a ring,
Ar$^1$, Ar$^2$ and Ar$^3$ are phenyl groups,
R$^1$ to R$^8$ are, respectively, hydrogen atoms or deuterium atoms, and
R$^9$ is a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group or an aryloxy group.

2. The compound having the indolocarbazole ring structure according to claim 1, of the following formula (1a),

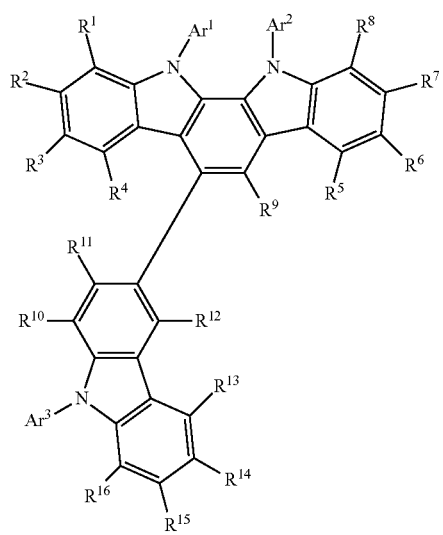

(1a)

wherein,

Ar¹ to Ar³ and R¹ to R⁹ are as defined in the above general formula (1), and

R¹⁰ to R¹⁶ are, respectively, hydrogen atoms, deuterium atoms, fluorine atoms, chlorine atoms, cyano groups, nitro groups, alkyl groups having 1 to 6 carbon atoms, cycloalkyl groups having 5 to 10 carbon atoms, alkenyl groups having 2 to 6 carbon atoms, alkyloxy groups having 1 to 6 carbon atoms, cycloalkyloxy groups having 5 to 10 carbon atoms, monovalent aromatic hydrocarbon groups, monovalent aromatic heterocyclic groups or aryloxy groups.

3. The compound having the indolocarbazole ring structure according to claim 1, wherein R⁹ in the above formula (1) is a hydrogen atom, a deuterium atom or a phenyl group.

* * * * *